(12) United States Patent
Johnston et al.

(10) Patent No.: US 7,312,202 B2
(45) Date of Patent: Dec. 25, 2007

(54) RATIONALLY DESIGNED AND CHEMICALLY SYNTHESIZED PROMOTER FOR GENETIC VACCINE AND GENE THERAPY

(75) Inventors: Stephen Johnston, Dallas, TX (US); Bao-Xi Qu, Plano, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 250 days.

(21) Appl. No.: 10/781,055

(22) Filed: Feb. 18, 2004

(65) Prior Publication Data

US 2004/0171573 A1 Sep. 2, 2004

Related U.S. Application Data

(60) Provisional application No. 60/448,166, filed on Feb. 18, 2003.

(51) Int. Cl.
C07H 21/04 (2006.01)
A01N 43/04 (2006.01)

(52) U.S. Cl. .................. 514/44; 536/24.1
(58) Field of Classification Search ............ None
See application file for complete search history.

(56) References Cited

U.S. PATENT DOCUMENTS

| | | | |
|---|---|---|---|
| 4,683,202 A | 7/1987 | Mullis | 435/91 |
| 5,717,058 A * | 2/1998 | Matthews et al. | 530/328 |
| 5,928,906 A | 7/1999 | Köster et al. | 435/91.2 |
| 6,410,210 B1 | 6/2002 | Gabriel | 430/315 |
| 6,410,241 B1 * | 6/2002 | Sykes et al. | 435/6 |
| 6,461,606 B1 * | 10/2002 | Flotte et al. | 424/93.2 |
| 6,525,189 B1 * | 2/2003 | Kim | 536/24.1 |
| 6,900,018 B2 * | 5/2005 | Sykes et al. | 435/6 |
| 7,018,833 B2 * | 3/2006 | Sykes et al. | 435/320.1 |
| 7,018,836 B1 * | 3/2006 | Price | 435/325 |
| 2002/0055173 A1 * | 5/2002 | Parks et al. | 435/456 |
| 2002/0146733 A1 * | 10/2002 | Sykes et al. | 435/6 |
| 2002/0150940 A1 * | 10/2002 | Sykes et al. | 435/6 |
| 2002/0155508 A1 * | 10/2002 | Sykes et al. | 435/7.2 |
| 2002/0160402 A1 * | 10/2002 | Sykes et al. | 435/6 |
| 2003/0104356 A1 * | 6/2003 | Berger | 435/5 |
| 2003/0129169 A1 * | 7/2003 | Krohn et al. | 424/93.21 |
| 2003/0186424 A1 * | 10/2003 | Roninson et al. | 435/235.1 |

OTHER PUBLICATIONS

Morral N, O'Neal W, Zhou H, Langston C, Beaudet A. 1997. Immune responses to reporter proteins and high viral dose limit duration of expression with adenoviral vectors: comparison of E2a wild type and E2a deleted vectors. Hum Gene Ther. Jul. 1;8(10):1275-86.*

Hoag H, Gore J, Barry D, Mueller C. 1999.Gene therapy expression vectors based on the clotting Factor IX promoter. Gene Ther. Sep.;6(9):1584-9.*

K Struhl-. 1995. Yeast Transcriptional Regulatory Mechanisms Annu Rev Genet. 5vol. 29: 651-674.*

Wahren B, Ljungberg K, Rollman E, Levi M, Zuber B, Kjerrstrom Zuber A, Hinkula J, Leandersson AC, Calarota S, Hejdeman B, Bratt G, Sandstrom E. 2002. HIV subtypes and recombination strains-strategies for induction of immune responses in man.Vaccine. May 6;20(15):1988-93.*

Barry et al., "Protection against mycoplasma infection using expression-library immunization," *Nature*, 377(6550):632-635, 1995.

Breathnack and Chambon, "Organization and expression of eucaryotic split genes coding for proteins," *Annu. Rev. Biochem.*, 50:349-383, 1981.

Burke et al., "The DPE, a conserved downstream core promoter element that is functionally analogous to the TATA box," *Cold Harbor Symposia on Quantitative Biology*, vol. LXIII, 75-82, The Mechanisms of Transcription, 1998.

Faisst and Meyer, "Compilation of vertebrate-encoded transcription factors," *Nucleic Acids Research*, 20(1):3-26, 1992.

Fujita et al., "Delimitation and properties of DNA sequences required for the regulated expression of human interferon-β gene," *Cell*, 41(2):489-496, 1985.

Fynan et al., "DNA vaccines: protective immunizations by parenteral, mucosal, and gene-gun inoculations," *Proc. Natl. Acad. Sci., USA*, 90:11478-11482, 1995.

Graves et al., "Homologous recognition of a promoter domain common to the MSV LTR and the HSV tk gene," *Cell*, 44(4):565-576, 1986.

Gronostajski, "Site-specific DNA binding of nuclear factor I: effect of the spacer region," *Nucleic Acids Research*, 15(14):5545-5559, 1987.

Harms and Splitter, "Interferon-γ inhibits transgene expression driven by SV40 or CMV promoters but augments expresion driven by the mammalian MHC I promoter," *Hum. Gene. Ther.*, 6(10):1291-1297, 1995.

Hu et al., "Transcriptional factor AP-4 contains multiple dimerization domains that regulate dimer specificity," *Genes Dev.*, 4(10):1741-1752, 1990.

Kadonaga et al., "Isolation of cDNA encoding transcription factor Sp1 and functional analysis of the DNA binding domain," *Cell*, 51(6):1079-1090, 1987.

Liu and Green, "A specific member of the ATF transcription factor family can mediate transcription activation by the adenovirus E1a protein," *Cell*, 61(7):1217-1224, 1990.

(Continued)

*Primary Examiner*—Celine Qian
*Assistant Examiner*—Laura M Mitchell
(74) *Attorney, Agent, or Firm*—Fulbright & Jaworski, L.L.P.

(57) ABSTRACT

The present invention relates to chemically synthesized promoters that circumvent the disadvantages of the universal CMV promoter/enhancer elements. The promoter may be used in a variety of applications, particularly in genetic immunization. The chemically synthesized promoter overcomes the common problems of the CMV promoter element such as: low transgene expression levels, transient expression, and the large amount of plasmid DNA needed for intramuscular injection in subjects.

3 Claims, 10 Drawing Sheets

OTHER PUBLICATIONS

McDonnel and Askari., "Molecular medicine," *New Engl. J. Med.*, 334(1):42-45, 1996.

Mitchell and Tijian, "Transcriptional regulation in mammalian cells by sequence-specific DNA binding proteins," *Science*, 245(4916):371-378, 1989.

Pardoll et al., "Exposing the immunology of naked DNA vaccines," *Immunity*, 3:165-169, 1995.

Perlmann et al., "Determination for selective RAR and TR recognition of direct repeat HREs," *Genes Dev.*, 7B:1411-1422, 1993.

Pollock et al., "Human SRF-related proteins: DNA-binding properties and potential regulatory targets," *Genes Dev.*, 5(12A):2327-2341, 1991.

Qin et al., "Promoter attenuation in gene therapy: interferon-$\gamma$ and tumor necrosis factor-$\alpha$ inhibit transgene expression," *Hum. Gene Ther.*, 8(17):2019-2029, 1997.

Ritter et al., "Stimulatory and inhibitory action of cytokines on the regulation of hCMV-IE promoter activity in human endothelial cells," *Cytokine*, 12(8):1163-1170, 2000.

Robinson, "DNA based vaccines: new possibilities for disease prevention and treatment," *Can. Med. Assoc. J.*, 152(10):1629-1632, 1995.

Ruvkun and Finney, "Regulation of transcriptional and cell identity by POU domain proteins," *Cell*, 64(3):475-478, 1991.

Smale and Baltimore, "The 'initiator' as a transcription control element," *Cell*, 57(1):103-113, 1989.

Spooner et al., "DNA vaccination for cancer treatment," *Gene Therapy*, 2:173-180, 1995.

Tanaka et al., "Recognition DNA sequences of interferon regulatory factor 1 (IRF-1) and IRF-2, regulators of cell growth and the interferon system," *Mol. Cell. Biol.*, 13(8):4531-4538, 1993.

Virbasius, "NRF-1, an activator involved in nuclear-mitochondrial interactions, utilizes a new DNA-binding domain conserved in a family of developmental regulators," *Genes Dev.*, 7(12A):2431-2445, 1992.

Williams and Tijian, "Analysis of the DNA-binding and activation properties of the human transcription factor AP-2," *Genes Dev.*, 5(4):670-682, 1991.

Yen et al., "An alternative spliced form of FosB is a negative regulator of transcriptional activation and transformation by Fos proteins," *Proc. Natl. Acad. Sci., USA*, 88(12):5077-5081, 1991.

\* cited by examiner

RATIONALLY DESIGNED AND CHEMICALLY SYNTHESIZED PROMOTER FOR GENETIC VACCINE AND GENE THERAPY

The present application claims the benefit of co-pending U.S. Provisional Patent Application Ser. No. 60/448,166, filed Feb. 18, 2003, the entire disclosure of which is specifically incorporated herein by reference.

The government owns rights in the present invention pursuant to DARPA grant Number N65236-99-1-5426.

BACKGROUND OF THE INVENTION

1. Field of the Invention

The present invention relates generally to the fields of immunology and molecular biology. More particularly, it concerns improved protective and immunotherapeutic vaccines.

2. Description of Related Art

The most frequently used promoters in the production of a genetic vaccine for humans are viral in origin. Examples of such viral promoters include but are not limited to Mouse Mammary Tumor Virus (MMTV) promoter, Human Immunodeficiency Virus Long Terminal Repeat (HIV LTR) promoter, Moloney virus, avian leukosis virus (ALV), Cytomegalovirus (CMV) immediate early promoter/enhancer, Rous Sarcoma Virus (RSV), adeno-associated virus (AAV) promoters; adenoviral promoters, and Epstein Barr Virus (EBV) promoters. One of the drawbacks of viral promoters is their tendency to be silenced when there is an immunological response. It has been shown that many commonly used viral promoters are silenced by interferons and TNF-alpha at the level of mRNA stability (Qin et al., 1997). Compatibility of viral promoters with certain antigens appears to affect gene expression levels of these promoters. Other factors that appear to affect the level of gene expression are introns (e.g. CMV intron A), as well as, polyadenylation sequences such as Bovine Growth Hormone (BGH) or SV40 versions.

Of the regulatory elements known to the skilled artisan, the cytomegalovirus (CMV) immediate-early promoter/enhancer, is the most commonly used in gene therapy and in genetic (DNA-based) vaccines. The CMV promoter exhibits strong activity in various cell lines in vitro. In genetic vaccines, the CMV promoter drives a high level of gene expression and can successfully elicit protective immune responses in various animal hosts. However, one of the common problems encountered by investigators is that transgenes are expressed only at a low level and only transiently. Another major caveat of the CMV promoter lies in the large amount of plasmid DNA needed for intramuscular injection in primates (including humans) to render it effective for the purpose of genetic immunization. Although the molecular mechanisms that are responsible for poor expression of the CMV promoter in primates are poorly defined, it could be mainly due to attenuation of the promoter. Thus, in current approaches utilizing CMV promoter/enhancer elements, genetic vaccines have proven to be inefficient in primates. Therefore, a more efficient promoter is required to circumvent the deficiencies of the CMV promoter as a genetic (DNA-based) vaccine.

DNA vaccines represent an emerging field that relates to the art of preventing and treating disorders, diseases, conditions and infections by inducing immune responses in individuals directed at antigens associated with such disorders, diseases, conditions and infections. Specifically, plasmid DNA and linear and circular elements that include coding sequences for antigens operably linked to regulatory elements required for gene expression is administered to individuals. It is noted that the antigens need not be physically linked to the regulatory elements. The cells of the individual take up the plasmid DNA and the coding sequence is expressed. The antigen so produced becomes a target against which an immune response is directed. The immune response directed against the antigen provides the prophylactic or therapeutic benefit to the individual against any allergen, pathogen, cancer cell or autoimmune cell that includes an epitope which is recognized by the immune response against the antigen.

DNA vaccines include naked and facilitated vaccines. Further, they may be administered by a variety of techniques that include several different devices and compositions for administering substances to tissue. The published literature includes several review articles that describe aspects of DNA vaccine technology (McDonnel et al., 1996; Robinson. 1995; Fynan et al., 1995; Pardoll et al., 1995; Spooner et al. 1995).

Although CMV DNA-based vaccines could be effective in eliciting an immune response in some cases, their major drawback lies in their diminished efficacy in some hosts, particularly humans. Therefore, there is a need for compositions and methods that produce an enhanced and effective immune response.

SUMMARY OF THE INVENTION

The present invention overcomes the deficiencies in the prior art by rationally designing and chemically synthesizing artificial promoters. Therefore, in accordance with the present invention, provided herein is a nucleic acid segment comprising a synthetic promoter/enhancer, or the complement of such a promoter/enhancer.

In particular embodiments, the nucleic acid segment of the present invention is optimized for use in genetic immunization and/or gene therapy. In another embodiment, the nucleic acid segment comprises a promoter sequence comprising regions encoding promoter elements including a TATA box, a TFIIB binding element, an initiator, a downstream promoter element, and an upstream binding element. In further embodiments the nucleic acid segment is further defined as comprising, as an upstream binding element, at least an IRF binding element. In yet another embodiment, the nucleic acid segment of the present invention comprising a promoter sequence is further defined as comprising as upstream binding elements, at least an SP1 binding element and an IRF binding element. In still yet another embodiment, the nucleic acid segment of the invention is further defined as comprising as upstream binding elements, at least an SP1 binding element, an α-interferon regulatory factor 1 (IRF-1) binding element, a CBP binding element, and NFκB binding element, and an AP1 binding element.

In other particular embodiments, the nucleic acid segment of the present invention is further defined as comprising an enhancer sequence comprising one or more additional binding elements selected from the group consisting of the SP1, IRF, CBP, AP1, c-Jun, NFκB, CREB/ATF, and NF1 binding elements. In yet another embodiment, the nucleic acid segment is further defined as comprising at least one spacer region between two or more regions encoding a promoter element and/or an enhancer element. In still yet another embodiment, the spacer region of the nucleic acid segment has no protein binding activity. In further embodiments, the spacer region has an approximately equal distribution of adenine, guanine, cytosine, and thymine bases. The spacer region of the present invention may further comprise three consecutive adenine bases or three consecutive thymine bases.

The nucleic acid segment of the present invention, is further defined as comprising the sequence of SEQ ID NO:35, SEQ ID NO:36 or SEQ ID NO:37.

In particular embodiments, the nucleic acid segment of the present invention is further defined as comprising a nucleic acid segment encoding or potentially encoding an immunogenic peptide or polypeptide. In other embodiments, the immunogenic polypeptide is HIV gp120.

The nucleic acid segment of the present invention is further defined as a linear or circular expression element. In other embodiments, the nucleic acid segment is further defined as a vector. The vector in some embodiments is further defined as a genetic immunization vector, a viral vector, a plasmid vector, a phagemid, a cosmid, or a BAC.

The nucleic acid segment of the present invention is further defined as being comprised in a pharmaceutical composition.

The present invention further embodies a nucleic acid segment comprising a promoter sequence comprising regions encoding promoter elements including a TATA box, a TFIIB binding element, an initiator, a downstream promoter element, and an upstream binding element.

The present invention also provides a method of expressing a polypeptide in a subject comprising: (a) obtaining a first nucleic acid segment comprising a region encoding a synthetic promoter/enhancer; (b) obtaining a second nucleic acid segment comprising a region encoding the polypeptide; (c) operatively linking the first nucleic acid to the second nucleic acid to form a construct comprising at least the region encoding the promoter and the region encoding the polypeptide; and (d) administering the construct to the subject. In some embodiments, the method of expressing a polypeptide in a subject comprises optimizing the promoter/enhancer for use in genetic immunization and/or gene expression. In another embodiment, the promoter/enhancer is further defined as comprising a promoter sequence comprising regions encoding promoter elements including a TATA box, a TFIIB binding element, an initiator, a downstream promoter element, and an upstream binding element. In yet another embodiment, the promoter sequence is further defined as comprising, as upstream binding elements, at least an SP1 binding element, an α-interferon regulatory factor 1 (IRF-1) binding element, a CBP binding element, and NFκB binding element, and an AP1 binding element. In further embodiments, the method of expressing a polypeptide in a subject is further defined as comprising an enhancer sequence comprising one or more additional binding elements selected from the group consisting of the SP1, IRF, CBP, AP1, c-Jun, NFκB, CREB/ATF, and NF1 binding elements. In still yet another embodiment, the method of expressing a polypeptide in a subject is further defined as a method of genetic immunization. In other embodiments, the subject is immunized against the peptide or polypeptide.

The method of expressing a polypeptide in a subject is further defined as a method of expression library immunization. The construct of the present invention is further defined as a linear or circular expression element in some embodiments and as a vector in other embodiments. In further embodiments, the construct of the present invention is further defined as being comprised in a pharmaceutical composition prior to administration to the subject.

The present also provides a method of expressing a polypeptide in a subject such as a mammal, which may be a human or a mouse.

As is used herein, "SRE" refers to the "sterol response element" and is denoted as "sterol response element" or "SRE". In cases where the "serum response element" is referred to, it is denoted as "serum response element".

BRIEF DESCRIPTION OF THE DRAWINGS

The following drawings form part of the present specifications and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
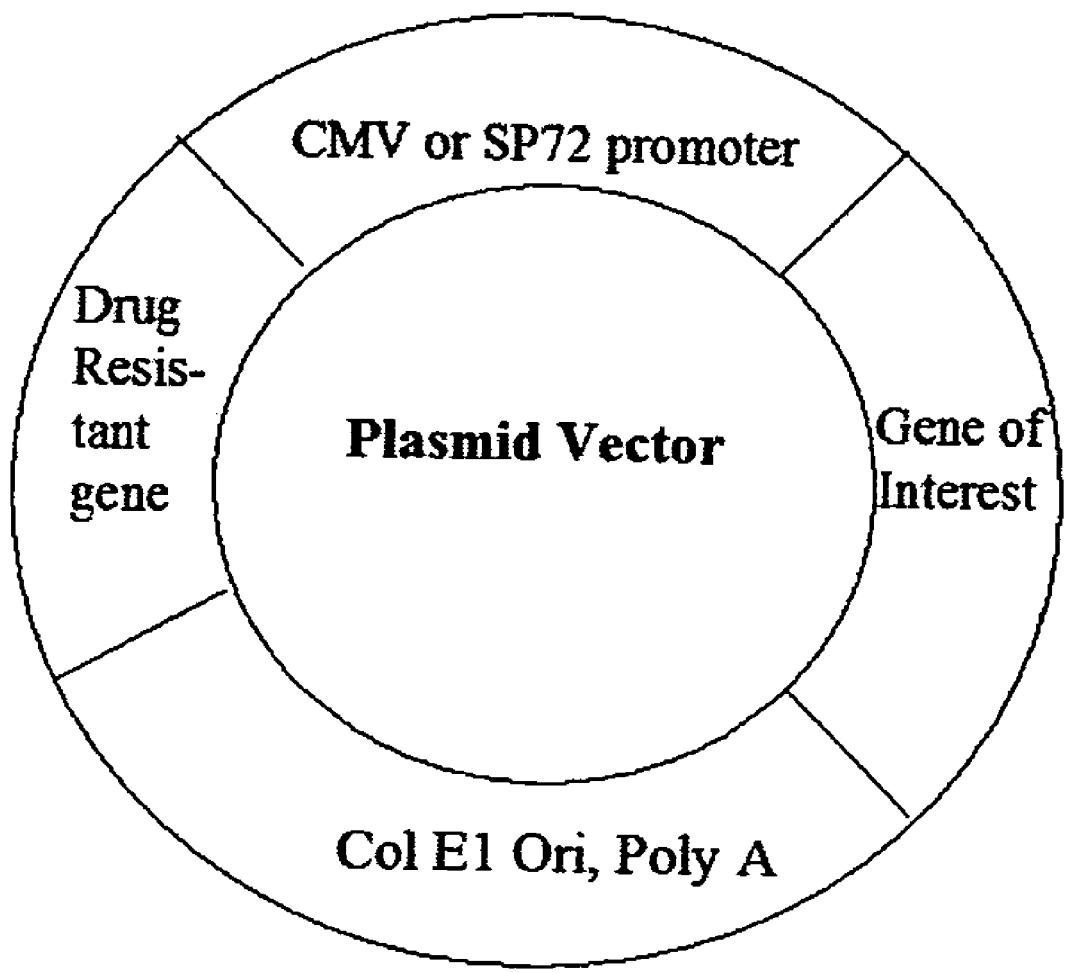
FIG. 1. Structure of plasmid DNA.

The present invention provides methods of chemically synthesizing a promoter that is more efficiently expressed in cells and overcomes the caveats of a universally used promoter such as the CMV promoter. Moreover, the present invention can be more efficiently used to express genes and antigens and furthermore provides an improved method for genetic immunization over that of the CMV promoter. cl I. The Present Invention The present invention overcomes problems of the CMV promoter and other known promoters, and increases the efficacy of genetic immunization. Limitations of biological promoters such as variations that can be introduced in vitro by site directed mutagenesis, restriction-fragment shuffling, or other enzymatic modification schemes do not exist for synthetic promoters, wherein a promoter is "made to order". Synthetic promoters based on the present invention are rationally designed and chemically synthesized to combine the best features of both synthetic and biological promoters. Synthetic oligos are annealed and ligated through several processes to generate the full-length chemically synthesized promoter.

One example of a promoter sequence useful in the preparation of a promoter/enhancer, according to the invention is provided as SEQ ID NO:35. This exemplary promoter comprises several binding elements of IRF-1, AP1; NFkB, SP1; CBP; TFIIB, AP2; the TATA box (TFIID); an initiator; and a downstream promoter element. These elements together comprise a 190 base pairs DNA segment. An example of a rationally designed and chemically synthesized artificial promoter/enhancer, which encompasses the exemplary promoter of SEQ ID NO:35, is represented by SEQ ID NO:36. Several promoter elements as is known to the skilled artisan were utilized in the chemical synthesis of the promoter "SP72". These elements may include at least one of an upstream enhancer element such as: a vitamin D binding element; a serum response element; a CREB/ATF element, a Myb element reversed; an AP4 element; an AP1 element; an Octamer element; an AP2 element; an ISRE reversed; a CTF-NF1; a CBP element; an SP1 element; c-Jun; NFκB; interferon regulatory factor-1 (IRF-1); TFIID; an initiator; and a downstream promoter element (DPE). In some embodiments, the promoter may be comprised in a promoter/enhancer lacking a sterol response element (SRE), such as that in SEQ ID NO:37, which is the sequence of SEQ ID: NO:36, less the sterol response element (SRE).

As describe herein, the promoters/enhancers of the invention can exhibit strong activity in cells, and can elicit a higher immune response in mice inoculated with the gene gun, microprojectile bombardment method than the commonly utilized CMV promoter. The overall advantage of the present invention therefore lies in the chemical synthesis of a promoter/enhancer that is more efficient in gene therapy and in genetic (DNA-based) vaccines than the currently used natural promoter such as the CMV promoter. This invention therefore embodies the function of a chemically synthesized promoter/enhancer in genetic immunization.

II. Nucleic Acid Molecules

A. Nucleic Acid Segment Comprising a Chemically Synthetic Promoter/Enhancer and its Constructs The invention involves the chemical synthesis of promoter/enhancers. In chemically synthesizing such promoters/enhancers, the desired sequence(s) may be made from synthetic oligos. For example, 60-mer oligonucleotides underwent several annealing and ligation processes in order to generate the SP72 promoter/enhancer as represented by (SEQ ID NO:36). The present invention further concerns a nucleic acid comprising a promoter sequence, that is a DNA sequence that contains elements which bind basal transcription machinery, including a TATA box, TFIIB recognition element, one or more SP-1 and one or more IRF-1, an initiator, and a downstream promoter element. The sequence further comprises an enhancer region that binds proximal and distal auxiliary factors.

Nucleic acid segments of the present invention may be derived from several annealing and ligation processes of synthetic oligomers of a number of elements as is known to the skilled artisan, which may include but are not limited to promoter binding elements or other binding elements, upstream binding elements, downstream elements, and an initiator.

A nucleic acid generally refers to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). A nucleic acid may also comprise of modified bases as are known to those of skill in the art. The term nucleic acid encompasses the terms oligonucleotide and polynucleotide. The term oligonucleotide refers to at least one molecule of between about 3 and about 100 nucleobases in length. The term polynucleotide refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

It is contemplated that the nucleic acid constructs of the present invention may regulate gene expression of an immunogenic polypeptide. A nucleic acid segment may regulate the expression of a full-length polypeptide sequence with additional heterologous coding sequences, for example to allow for therapeutic benefits such as targeting or efficacy.

In a non-limiting example, one or more nucleic acid constructs may be prepared that include a contiguous stretch of nucleotides identical to or complementary to, for example, the promoters/enhancers, of the present invention. Such a nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome as are known to those of ordinary skill in the art. It will be readily understood that intermediate lengths and intermediate ranges, as used herein, means any length or range including or between the quoted values (i.e., all integers including and between such values).

1. Promoter Elements of a Chemically Synthetic Promoter

A promoter/enhancer, such as in the present invention, may further be defined as a control sequence that is a region of a nucleic acid sequence at which transcriptional initiation and the rate of transcription are controlled. A promoter generally comprises a nucleic acid sequence that functions to position the start site for RNA synthesis. The best known example of this is the TATA box.

As in the present invention, the nucleic acid segment of a chemically synthesized promoter/enhancer may comprise regions encoding promoter elements such as a TATA box, a TFIIB recognition element, an upstream binding element, an initiator, and a downstream promoter element. The core of the promoter may include a TATA box, upstream binding elements (TF1B, SP1 and at least one IRF-1 response elements), and other downstream binding elements as are known to the skilled artisan.

A chemically synthesized promoter/enhancer of the invention may further consist of various binding elements to optimize transcriptional regulation. Examples of these elements are: a vitamin D binding element; a serum response element; CREB/ATF element, Myb element reversed; AP4 element; AP1 element; Octamer element; AP2 element; ISRE reversed; CTF-NF1; CBP element; SP1 element; c-Jun; NFκB; α-IFN; and TFIID (Table 1). These elements may be derived from a variety of sources such as viral, bacterial and/or mammalian as known and selected by those of skill in the art.

The spacing between promoter elements frequently is flexible in terms of length, so that promoter function is preserved when elements are inverted or moved relative to one another. For example, in the thymidine kinase (tk) promoter the spacing between promoter elements can be increased to 50 bp apart before activity begins to decline. As in the present invention, the spacing region between two or more regions encoding the promoter elements may not have transcription factor binding activity. Additionally, as discussed elsewhere in this specification, the spacing region may have approximately equal distribution of adenine, guanine, cytosine and thymine bases and may further be comprised of a number of consecutive adenine or thymine bases.

Depending on the promoter, individual elements can function either cooperatively or independently to activate transcription. Furthermore, a promoter may or may not be used in conjunction with an enhancer, which refers to a cis-acting regulatory sequence involved in the transcriptional activation of a nucleic acid sequence. It is noted, that the enhancer can be distinguished from a promoter by two characteristics: 1) the position of an enhancer need not be fixed; it can be placed upstream, downstream, or within the gene it regulates; 2) its orientation can be inverted without impeding its activity; and 3) an enhancer can function in trans as well as in cis.

In addition to producing nucleic acid segments of promoters and enhancers by chemical synthesis, sequences may be produced using recombinant cloning and/or nucleic acid amplification technology, including PCR™, in connection with the compositions disclosed herein (U.S. Pat. Nos. 4,683,202 and 5,928,906, each incorporated herein by reference).

TABLE 1

BINDING ELEMENTS

| SEQUENCE | AUTHOR/YEAR | NO |
|---|---|---|
| Vitamin D binding | Perlmann et al 1993 | 1 |
| Serum response | Pollock et al 1991 | 2 |
| CREB/ATF | Liu and Green 1990 | 3 |
| Myb (reverse) | Faisst and Meyer 1992 | 4 |
| AP4 | Hu et al 1990 | 5 |
| AP1 | Yen et al 1991 | 6 |
| CTF-NF1 | Gronostajski 1987 | 7 |
| (CTF-NFI) Octamer | Ruvkun and Finney 1991 | 8 |
| AP2 | Williams and Tijina 1991 | 9 |
| ISRE reverse | Tanaka et al 1993 | 10 |
| CTF-NF1 | Gronostajski 1987 | 11 |
| CPB | Graves et al 1986 | 12 |
| SP1 | Kadonaga et al 1987 | 13 |
| CREB/ATF | Liu and Green 1990 | 14 |
| C-Jun | Mitchell and Tijian 1989 | 15 |
| CBP | Graves et al 1986 | 16 |
| NFκB | Virbasius 1993 | 17 |
| AP1 | Yen et al 1991 | 18 |
| NFκB | Virbasius, 1993 | 19 |
| c-Jun | Mitchell and Tjian 1989 | 20 |
| SP1 | Kadonaga et al 1987 | 21 |
| α-IFN | Fujita et al 1985 | 22 |
| AP1 | Yen et al 1991 | 23 |
| α-IFN | Fujita et al 1985 | 24 |
| NFκB | Virbasius, 1993 | 25 |
| SP1 | Kadonaga et al 1987 | 26 |
| CBP | Graves et al 1986 | 27 |
| SP1 | Kadonaga et al 1987 | 28 |
| TFIIB | Breathnack and Chambon 1981 | 29 |
| TFIID | Breathnack and Chambon 1981 | 30 |
| Initiator | Smale and Baltimore, 1989 | 31 |
| AP2 | Williams and Tijian 1991 | 32 |
| Downstream element | Burke et al 1998 | 33 |
| GAGCTCTCAGTCTCAGCGA TCAA (SEQ ID NO:34) | | 34 |

2. Initiation Signals

A specific initiation signal also may be required for efficient transcription of mRNA from DNA. The initiator sequence positioned downstream of the TATA box could be helpful in directing specific transcription initiation. Various initiation elements have been described and classified according to sequence homology. These initiation elements are recognized specifically by initiator-binding proteins. Interaction between these initiator binding proteins and components of the basal transcription machinery provides a means through which a transcription competent complex can be formed and transcription can be initiated.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

B. Nucleic Acid Segments Encoding a Polypeptide Encoding Sequence Under the Control of a Chemically Synthesized Promoter/Enhancer In some embodiments, a nucleic acid segment of the present invention may comprise a nucleic acid segment encoding a polypeptide under the control of the inventive synthetic promoters and/or promoters/enhancers. Such polypeptides may be created via the application of recombinant DNA technology, in which changes in the protein structure may be engineered, based on considerations of the properties of the amino acids being exchanged. Changes designed by humans may be introduced through the application of site-directed mutagenesis techniques (as described herein), or may be introduced randomly and screened later for the desired function. These changes may require manipulation of codons.

Codons are DNA triplets that constitute "one information unit" for protein synthesis; 64 distinct triplet sequences exist. The 20 amino acids are encoded by 61 codons and the remaining 3 codons encode protein synthesis termination signals. Each codon is specific for a single amino acid (Table 2). In most cases, however, a single amino acid can be identified by more than one codon. Thus different DNA sequences can code for the same protein.

TABLE 2

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |

TABLE 2-continued

| Amino Acids | | | Codons |
|---|---|---|---|
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

III. Site-Directed Mutagenesis

One way of manipulating nucleic acid segments comprising promoters/enhancers of the present invention is by site-directed, or site-specific mutagenesis. Site-specific mutagenesis is a technique for specific mutagenesis of DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Techniques for site-directed mutagenesis are known to those of skill in the art, and can be practiced without undue experimentation in the context of the invention.

IV. Delivery of a Nucleic Acid Constructs of Promoter/Enhancers

A. Vectors

Two broad approaches have been used to employ vectors to deliver nucleic acids to cells, namely viral vectors and non-viral vectors. As by methods described herein and as is known to the skilled artisan, expression vectors may be constructed to deliver nucleic acids comprising the promoters/enhancers of the present invention to a organelle, cell, tissue, or an organism. Such vectors comprising the inventive promoters may be used in a variety of manner consistent with the invention, including in screening assay and genetic immunization protocols.

A vector in the context of the present invention refers to a carrier nucleic acid molecule into which a nucleic acid sequence of the present invention may be inserted for introduction into a cell and thereby replicated. A nucleic acid sequence can be exogenous, which means that it is foreign to the cell into which the vector is being introduced; or that the sequence is homologous to a sequence in the cell but positioned (i.e. integrated) within the host cell nucleic acid in which the sequence is ordinarily not found. Vectors include plasmids; cosmids; viruses such as bacteriophage, animal viruses, and plant viruses; and artificial chromosomes (e.g., YACs, MACs); and synthetic vectors such as linear/circular expression elements (LEE/CEE). One of skill in the art would be well equipped to construct any number of vectors through standard recombinant techniques as described in Maniatis et al., 1990 and Ausubel et al., 1994, and Sambrook 2000, incorporated herein by reference.

An expression vector refers to any type of genetic construct comprising a nucleic acid coding for an RNA capable of being transcribed. In the context of the present specification, expression vectors will typically comprise the synthetic promoters described herein. In some cases, RNA molecules (specifically, mRNA) are then translated into a protein, polypeptide, or peptide. In other cases, these sequences are not translated, as in the case of antisense molecules, small interfering RNA (siRNA) or ribozymes production. Expression vectors can contain a variety of control sequences, which refer to nucleic acid sequences necessary for the appropriate regulated transcription and possibly translation of an operably linked coding sequence in a particular host cell. In addition to control sequences that govern transcription and translation, vectors and expression vectors may contain nucleic acid sequences that serve other functions as well, and are described herein.

B. Linear and Circular Expression Elements

Linear and/or Circular Expression Elements (LEEs/CEEs) may also be employed as vehicles for delivering nucleic acids comprising promoter/enhancers of the present invention. LEEs or CEEs technology allows for a rapid and effective means by which to determine the activity of a particular gene product or its physiological responses, by circumventing the use of plasmids and bacterial cloning procedures. In certain embodiments, the promoter and terminator sequences of the LEE/CEE may be regarded as a type of vector, and may be used for any purpose for which a vector may be used, including genetic immunization.

LEEs and/or CEEs may be made according to the disclosure of U.S. Pat. No. 6,410,210, incorporated herein by reference.

Production of a LEE or CEE generally comprises obtaining a nucleic acid segment and linking the segment to a promoter, and a terminator, and/or other molecules such as a nucleic acid, to create an LEE or CEE. In producing LEEs and/or CEEs according to the present invention, the promoters and/or promoter/enhancers of the invention will be used. The nucleic acid segment, terminator and/or additional nucleic acid(s) may be obtained by any method described herein or as would be known to one of ordinary skill in the art, including by nucleic acid amplification or chemical synthesis of nucleic acids such as described in EP 266,032, incorporated herein by reference, or as described by Froehler et al., 1986, and U.S. Pat. No. 5,705,629, each incorporated herein by reference.

V. Methods of Delivery of Nucleic Acid Constructs Comprising Promoters

Suitable methods for delivery of nucleic acids comprising the inventive promoters and/or promoter/enhancers, for transformation of a cell, tissue, or organism for use with the current invention include virtually any method by which nucleic acids can be introduced into a cell, or an organism, as described herein or as would be known to one of ordinary skill in the art. Such methods include, but are not limited to: direct delivery of DNA by injection (U.S. Pat. Nos. 5,994, 624; 5,981,274; 5,945,100; 5,780,448; 5,736,524; 5,702, 932; 5,656,610; 5,589,466; and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al, 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783; 5,563,055; 5,550,318; 5,538,877; and 5,538,880, each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563, 055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed. In certain embodiments, acceleration methods are preferred and include, for example, microprojectile bombardment or inhalation methods.

VI. Genetic Immunization Using Nucleic Acid Constructs Comprising Promoters

The present invention further seeks to utilize nucleic acid segments comprising promoters/enhancers in gene therapy and DNA-based vaccines; hence, improving upon the efficacy of the heretofore essentially universally utilized CMV promoter. The technology for using DNA segments as vaccines is generally termed "Genetic Immunization" or "DNA Vaccination" (Cohen, 1993). It is now known that cells can take up naked DNA and express the peptides encoded on their surface, thus stimulating an effective immune response, which includes the generation of cytotoxic T lymphocytes (killer T cells). This technology is particularly suitable to protect against bacterial infections and is expected to be equally protective against viral infections. For example, immunization with DNA has been successfully employed to protect animals from challenge with influenza A (Ulmer et al., 1993). Other such examples in the art are well known to the skilled artisan.

Genetic immunization further provides a method in which nonreplicative plasmids are directly introduced into host cells to produce an immune response against the encoded foreign antigen. The utilization of this technology, and variations thereof, such as those described by Tang et al. (1992), Ulmer et al. (1993); Cox et al. (1993), Fynan et al. (1993), Wang et al. (1993) and Whitton et al. (1993), each incorporated herein by reference, is particularly suitable as it has already been shown to be successful in generating a specific immune response against a form of influenza virus. It is contemplated that virtually any type of vector, including naked DNA in the form of a plasmid, could be employed to generate an immune response in conjunction with a wide variety of immunization protocols, including parenteral, mucosal and gene-gun inoculations (Tang et al., 1992; Fynan et al., 1993).

In the present invention genetic immunization comprises introducing a nucleic acid comprising promoters/enhancers into a subject by microprojectile bombardment with a gene gun to elicit an immune response against a plasmid encoded foreign antigen (these include but are not limited to: human alpha-1 anti-trypsin (hAAT); and HIV gp-120). As is known to the skilled artisan, genetic immunization is generally practiced by either introducing plasmid DNA into skin by particle bombardment with the gene gun or into muscle by needle injection. The introduced plasmids and their antigen-encoded gene products are detected predominantly in keratinocytes and fibroblasts (FBs) after gene gun-mediated delivery and in muscle fibers after intramuscular injection.

As set forth in the present invention, genetic immunization involves expressing an immunogenic polypeptide in a subject comprising obtaining a first nucleic acid segment comprising a region encoding a promoter/enhancer optimized for use as a DNA vaccine; obtaining a second nucleic acid segment comprising a region encoding the polypeptide; operatively linking the first nucleic acid to the second nucleic acid to form a construct comprising at least the region encoding the promoter and the region encoding the polypeptide and, in most contemplated embodiments, a transcriptional terminator; and administering the construct to the subject.

In the present invention, a genetic vaccine for use in genetic immunization may further employ a promoter/enhancer comprising regions encoding elements which include: a TATA box, a TFIIB recognition element, an initiator and a downstream promoter element. The promoter/enhancer may further comprise at least one SP1 binding element and at least one IRF-1 binding elements. Additional binding elements may also be included such as CBP, NFκB, AP1, AP2, in any order but is not limited to these binding elements, As set forth in the present invention, genetic immunization involves generating an immune response by contacting a subject such as a mouse or a human with a nucleic acid segment of the present invention and further contacting said subject with a polypeptide against which an immune response is desired wherein the polypeptide is a hAAT polypeptide against which an immune response is desired. hAAT is a secreted protein that is a model antigen in genetic immunization for animal models in the laboratory. As is known to those skilled in the art, mice receiving standard genetic immunization with the hAAT gene are known to generate marked humoral responses, as well as significant CD8$^+$ T cell-mediated cytotoxicity, providing an opportunity to study both major histocompatibility complex class II- and class I-dependent immunity.

VII. Expression Library Immunization

The inventors have previously devised a method of identifying vaccines using a genomic expression library representing all of the antigenic determinants (except for those resulting from post-translational modification of the protein) of a pathogen. This method has broad application as a screening method and is further identified as an expression immunization library ("ELI"; U.S. Pat. Nos. 5,703,057 and 5,989,553). The method has the advantages of "gene immunization" by eliminating the potential for infection while also providing for a general and effective method of immunizing and identifying a vaccine without having to characterize the pathogen against which the vaccine is desired. ELI may therefore be employed in the present invention to further identify genetic vaccines for use with the promoters of the present invention.

The preparation of an expression library is performed using the techniques and methods familiar to the molecular biologist. The pathogen's genome, whether bacterial, yeast, mold, fungal, algal, protozoan, or viral, may or may not be known and may even have been cloned. Thus one obtains DNA (or cDNA) representing substantially the entire genome of the pathogen. The DNA is broken up, by physical fragmentation or restriction endonuclease digestion, into segments of some length so as to provide a library of about $10^{-1}$ (x genome size) members. Of course for cloned DNA in YACs, a sufficient library may be available. In cases, as for certain viruses, where the genome is RNA, the RNA may be used to prepare a DNA library. Alternatively, mRNA may be used to generate libraries; for example from human or animal tumor cells.

Once expression libraries have been prepared for a given pathogen and DNA plasmid libraries isolated, one will inoculate a mammal with a DNA plasmid library. The library may be inoculated into the animal in any one of several different methods that have been shown effective for genetic immunization; for example, gene gun or needle injection into muscle or skin or by oral administration or by inhalation. The gene gun technique used for ELI is thought to be approximately 1,000- to 10,000-fold more efficient than injection of naked DNA (Fynan, et al., 1993). Alternatively, others e.g Ulmer et al. (1993), have indicated the genetic immunization by direct DNA injection may be performed with similar efficiency as the gene gun. The inventors have found that gene administration by either method produces qualitatively identical immunization.

VIII. Pharmacological Preparations of Nucleic Acids of Promoters

A. Routes of Delivery/Administration

The preparation of vaccines, as in the present invention, which may contain nucleic acid segments comprising promoters/enhancers determined from the DNA of plasmids identified as protective against pathogen challenge as active ingredients, is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions or solid forms suitable for solution in, or suspension in, liquid prior to injection. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

Vaccines may be conventionally administered parenterally, by injection, for example, subcutaneously, intramuscularly or intradermally The manner of application may be varied widely. Any of the conventional methods for administration of a vaccine are applicable. These are believed to include gene gun inoculation of the DNA encoding the antigen peptide(s), phage transfection of the DNA, oral application on a solid physiologically acceptable base or in a physiologically acceptable dispersion, parenterally, by injection or the like. The dosage of the vaccine will depend on the route of administration and will vary according to the species and size of the host.

Various methods of achieving adjuvant effect for the vaccine includes use of agents such as aluminum hydroxide (alum) or aluminum phosphate, commonly used as about 0.05 to about 0.1% w/v solution in phosphate buffered saline, admixture with synthetic polymers of sugars (CARBOPOL®) used as an about 0.25% solution w/v, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *Cryptosporidium parvum* or endotoxins or lipopolysaccharide components of Gram-negative bacteria, emulsion in physiologically acceptable oil vehicles such as mannide mono-oleate (Aracel A) or emulsion with a 20% solution of a perfluorocarbon (FLUOSOL DA®) used as a block substitute may also be employed.

B. Administration of Nucleic Acid Vaccines

Compositions comprising nucleic acids comprising promoters/enhancers as in the present invention may also be administered parenterally, intravenously, intradermally, intramuscularly, transdermally or even intraperitoneally as described in U.S. Pat. Nos. 5,543,158; 5,641,515; and 5,399,363 (each specifically incorporated herein by reference in its entirety).

Injection of a nucleic acid comprising promoters/enhancers, of the present invention may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225). One method for the delivery of nucleic acids comprising promoters/enhancers as in the present invention is via gene gun injection. As known to the skilled artisan, the main methods of administration of DNA vaccines are via particle bombardment, achieved using a gene gun, via inhalation, or via intramuscular saline injection. For the gene gun method as employed by the present invention, the DNA is coated onto gold particles that are then fired into the target tissue which is usually the epidermis. Gene gun methods have been shown to be the most efficient as the same level of antibody and cellular immunity may be gained using 100-5000 fold less DNA than is necessary for injection methods (Pertmer et al., 1995; Fynan et al., 1993). Although the gene gun method is more efficient it has not been shown to have longer lived responses or provide better protection from pathogenic challenge than intramuscular vaccination (Cohen et al., 1998). The interesting difference between the two methods is that they elicit different Th responses biases. The intramuscular inoculation is associated with a Th-1 response producing elevated interferon gamma, little IL-4 and more IgG2a than IgG1 antibodies (Pertmer et al., 1996). The gene gun method, on the other hand, produces a Th-2 response, on successive immunizations, with the opposite cytokine and antibody profile to the intramuscular inoculation.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

A vaccination schedule and dosages may be varied on a subject by subject basis, taking into account, for example, factors such as the weight and age of the subject, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size and age of the host. Precise amounts of an active ingredient required to be administered depend on the judgment of the practitioner. In many instances, it will be desirable to have multiple administrations of the vaccine, usually not exceeding six vaccinations, more usually not exceeding four vaccinations and preferably one or more, usually at least about three vaccinations. The vaccinations will normally be at two to twelve week intervals, more usually from three to five week intervals. Periodic boosters at intervals of 1-5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with a nucleic acid can be performed, following immunization.

C. Combination Treatments

The compounds and methods of the present invention may be used in the context of diseases/conditions that include but are not limited to cancers and infectious and inflammatory diseases. In order to increase the effectiveness of a treatment with the compositions comprising the promoters of the present invention, it may be desirable to combine these compositions with other agents effective in the treatment of those diseases and conditions. For example, the treatment of a cancer may be implemented via genetic vaccination involving the promoters of the present invention and other anti-cancer therapies, such as anti-cancer agents or surgery. Likewise, the treatment of a vascular disease or condition may involve both nucleic acid comprising a chemically synthesized promoter of the present invention, and conventional agents or therapies. Alternatively, other diseases or conditions such as viral, inflammatory, parasitic, or infectious diseases (which include but is not limited to tuberculosis, hepatitis B, HIV-1, influenza, and malaria) may be treated with compositions and by methods of the present invention in combination with therapeutic agents typically employed in the treatment of the particular disease or condition.

Administration of expression constructs comprising the promoters of the present invention to a patient will follow general protocols for the administration of that particular secondary therapy, taking into account the toxicity, if any, of the chemically synthesized promoter treatment. It is expected that the treatment cycles would be repeated as necessary. It also is contemplated that various standard therapies, as well as surgical intervention, may be applied in combination with the therapy of the disease or condition.

IX. Examples

The following examples are included to demonstrate exemplary embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The promoter and enhancer parts of the exemplary chemically synthesized promoters disclosed herein were designed according to the currently available knowledge of the transcription mechanisms of RNA polymerase II and partly by trial of different combinations and permutations of the oligonucleotide sequences. Each construct was centered by a TATA box (Burke et al., 1998) (here TATATAA (SEQ ID NO:30); TFIID, Breathnach and Chambon 1981) with the initiator at position +1 (here TCATTC (SEQ ID NO:39), Initiator, Smale and Baltimore, 1989). Various transcription factors binding sites and other elements were added upstream and downstream of the TATA box in these exemplary examples. These sites and elements are underlined and indicated in parenthesis, after each specific sequence as in Examples 1, 2 and 3 below and Table 1. In the sequences described below lack of underlining represents spacing regions which may vary but usually follows the following rule as discussed elsewhere in the specification: the spacing region may have approximately equal distribution of adenine, guanine, cytosine and thymine bases and may further be comprised of three consecutive adenine or thymine bases.

Example 1

SP72 Promoter/Enhancer

To overcome the disadvantages of the CMV promoter, the inventors rationally designed and chemically synthesized an exemplary artificial promoter, designated SP72. SP72 is a 620 base pair DNA fragment. It was built by using twenty 60mer oligonucleotides that underwent several annealing and ligation processes. The full-length promoter was then ligated upstream of a reporter gene in a plasmid vector. The DNA fragment was cloned into a standard plasmid vector, pCMVi (Barry et al., 1995) by replacing the CMV promoter and its intron. The sequence of the SP72 promoter/enhancer (SEQ. ID NO:36) is as detailed below:

CGGTACATGATGTTCTCGATGCAATAT-CACGTGAAGGTCAAAAATAGGTCA (SEQ ID NO:1) (Vitamin D binding element, Perlmann et al., 1993) AGGTCACCTCTCTCGGCT (SEQ ID NO:2) (serum response element, Pollock et al., 1991) ATCAAATAA-GAGTGTAGGGACGGGAGAGGGGGAAAACAGAAC-AGAACAGTGCTGACGTCA (SEQ ID NO:3) (CREB/ATF element, Liu and Green, 1990) GCAGGCAGTTG (SEQ ID NO:4) (Myb element, reverse, Faisst and Meyer, 1992) CCCTTTGAAAA CGTTAACGTTAACGTT CAGCTGCAGCTGCA (SEQ ID NO:5) (AP4 element, Hu et al., 1990) GCTGATTAA (SEQ ID NO:6) (AP1, Yen et al., 1991) TAATTACAGCCAA (SEQ ID NO:7) (CTF-NFI, Gronostajski, 1987) AGGCGCCAAAGGCAACGTTATA TGCAAATATGCAAA (SEQ ID NO:8) (Octamer element, Ruvkun and Finney, 1991) TGAGAACAG GGGGGGGGGGCGG (SEQ ID NO:9) (AP2, Williams and Tjian, 1991) ACATCGGTTCAACGTTTCTGGTTTC AATTTCTCTTCT (SEQ ID NO:10) (ISRE reverse, Tanaka et al., 1993) ATTAATAATTACCGTTGGCCATTAGCCA (SEQ ID NO:11) (CTF-NF1, Gronostajski, 1987) TAT CCAAT (SEQ ID NO:12) (CBP element, Graves et al., 1986) GGGGCGGG (SEQ ID NO:13) (SP1, Kadonaga et al., 1987) ATTTGACGTCA (SEQ ID NO:14) (CREB/ATF, Liu and Green 1990) ATAATGAC (SEQ ID NO:15) (C-Jun, Mitchell and Tjian, 1989) GCCAAT (SEQ ID NO:16) (CBP element, Graves et al., 1986) AGGGACTTTCC (SEQ ID NO:17) (NFκB, Virbasius, 1993) GACTCAC (SEQ ID NO:18) (AP1, Yen et al., 1991) GGGGATTTC (SEQ ID NO:19) (NFκB element, Virbasius et al., 1993) CAAC GTTTTGGTTGACGAA (SEQ ID NO:20) (C-Jun element, Mitchell and Tjian, 1989) ATGGGCGG (SEQ ID NO:21) (SP1 element, Kadonaga, et al., 1987) TGTAAATGACATA (SEQ ID NO:22) (α-IFN, Fujita et al., 1985) GGAAAAC TGACTCA (SEQ ID NO:23) (AP1, Yen et al., 1991) CAAAGGGAGAAGTGA (SEQ ID NO:24) (α-IFN, Fujita et al., 1985) AAGTGGGACTTTCC (SEQ ID NO:25) (NFκB, Virbasius et al., 1993) AAAGGGCGG (SEQ ID NO:26) (SP1, Kadonaga, et al., 1987) CCAAT (SEQ ID NO:27) (CBP, Graves et al., 1986) TGTGGGCGGGG (SEQ ID NO:28) (SP1, Kadonaga, et al., 1987) CCACCGGTGT-TCCTGAAGGGCGCC (SEQ ID NO:29) (TFIIB) TATATAA (SEQ ID NO:30) (TFIID, Breathnach and Chambon, 1981) GGGGGGGCGGGCGCGTTCGTCCTCATTC (SEQ ID NO:31) (Initiator, Smale and Baltimore, 1989) TGGACCGCGTCCGCCCCGCG (SEQ ID NO:32) (AP2, Williams and Tjian, 1991) AGCAGACGTG (SEQ ID NO:33) (downstream element, Burke et al., 1998) GAGCTCTCAGTCTCAGCGATCAA (SEQ ID NO:34).

Example 2

SP72 Promotor/Enhancer Less the SRE (Serum Response Element)

The inventors generated a further exemplary promoter/enhancer sequence of SEQ. ID NO:37 using methods as is known to the skilled artisan and described herein, by deleting the SRE of the exemplary promoter/enhancer of SEQ. ID NO:36, thereby obtaining a further promoter/enhancer as detailed below:

CGGTACATGATGTTCTCGATGCAATATCACGTGA-AGGTCAAAAATAGGTCA (SEQ ID NO:1) (Vitamin D binding element, Perlmann et al., 1993) ATCAAATAA-GAGTGTAGGGACGGGAGAGGGGGAAAACAGAAC-AGAACAGTGCTGACGTCA (SEQ ID NO:3) (CREB/ATF element, Liu and Green, 1990) GCAGGCAGTTG (SEQ ID NO:4) (Myb element, reverse, Faisst and Meyer, 1992) CCCTTTGAAAACGTTAACGTTAACGTT CAGCTGCAGCTGCA (SEQ ID NO:5) (AP4 element, Hu et al., 1990) GCTGATTAA (SEQ ID NO:6) (AP1, Yen et al., 1991) TAATTACAGCCAA (SEQ ID NO:7) (CTF-NFI, Gronostajski, 1987) AGGCGCCAAAGGCAACGTTATA TGCAAATATGCAAA (SEQ ID NO:8) (Octamer element, Ruvkun and Finney, 1991) TGAGAACAG GGGGGGGGGGCGG (SEQ ID NO:9) (AP2, Williams and Tjian, 1991) ACATCGGTTCAACGTTTCTGGTTTC AATTTCTCTTCT (SEQ ID NO:10) (ISRE reverse, Tanaka et al., 1993) ATTAATAATTACCGTTGGCCATTAGCCA (SEQ ID NO:11) (CTF-NF1, Gronostajski, 1987) TAT CCAAT (SEQ ID NO:12) (CBP element, Graves et al, 1986) GGGGCGGG (SEQ ID NO:13) (SP1, Kadonaga et al., 1987) ATTTGACGTCA (SEQ ID NO:14) (CREB/ATF, Liu and Green 1990) ATAATGAC (SEQ ID NO:15) (C-Jun, Mitchell and Tjian, 1989) GCCAAT (SEQ ID NO:16) (CBP element, Graves et al., 1986) AGGGACTTTCC (SEQ ID NO:17) (NFκB, Virbasius, 1993) GACTCAC (SEQ ID NO:18) (AP1, Yen et al., 1991) GGGGATTTC (SEQ ID NO:19) (NFκB element, Virbasius et al., 1993) CAAC GTTTTGGTTGACGAA (SEQ ID NO:20) (C-Jun element, Mitchell and Tjian, 1989) ATGGGCGG (SEQ ID NO:21) (SP1 element, Kadonaga, et al., 1987) TGTAAATGACATA (SEQ ID NO:22) (α-IFN, Fujita et al., 1985) GGAAAAC TGACTCA (SEQ ID NO:23) (AP1, Yen et al., 1991) CAAAGGGAGAAGTGA (SEQ ID NO:24) (α-IFN, Fujita et al., 1985) AAGTGGGACTTTCC (SEQ ID NO:25) (NFκB, Virbasius et al., 1993) AAAGGGCGG (SEQ ID NO:26) (SP1, Kadonaga, et al., 1987) CCAAT (SEQ ID NO:27) (CBP, Graves et al., 1986) TGTGGGCGGGG (SEQ ID NO:28) (SP1, Kadonaga, et al., 1987) CCACCGGTGT-TCCTGAAGGGCGCC (SEQ ID NO:29) (TFIIB) TATATAA (SEQ ID NO:30) (TFIID, Breathnach and Chambon, 1981) GGGGGGGCGGGCGCGTTCGTCCTCATTC (SEQ ID NO:30) (Initiator, Smale and Baltimore, 1989) TGGACCGCGTCCGCCCCGCG (SEQ ID NO:32) (AP2, Williams and Tjian, 1991) AGCAGACGTG (SEQ ID NO:33) (downstream element, Burke et al., 1998) GAGCTCTCAGTCTCAGCGATCAA (SEQ ID NO:34).

Example 3

SP72 Promoter Sequence

In a further embodiment of the invention, the promoter sequence (SEQ. ID NO:35) of SP72 is provided, as detailed below:

AAATGACATA (SEQ ID NO:40) (α-IFN, Fujita et al., 1985) GGAAAACTGACTCA (SEQ ID NO:23) (AP1, Yen et al., 1991) CAAAGGGAGAAGTGA (SEQ ID NO:24) (α-IFN, Fujita et al., 1985) AAGTGGGACTTTCC (SEQ ID NO:25) (NFκB, Virbasius et al., 1993) AAAGGGCGG (SEQ ID NO:26) (SP1, Kadonaga, et al., 1987) CCAAT (SEQ ID NO:27) (CBP, Graves et al., 1986) TGT GGGCGGGG (SEQ ID NO:28) (SP1, Kadonaga, et al., 1987) CCACCGGTGTTCCTGAAGGGCGCC (SEQ ID NO:29) (TFIIB) TATATAA (SEQ ID NO:30) (TFIID, Breathnach and Chambon, 1981) GGGGGGGCGGGCG-CGTTCGTCCTCATTC (SEQ ID NO:31) (Initiator, Smale and Baltimore, 1989) TGGACCGCGTCCGCCCCGCG (SEQ ID NO:32) (AP2, Williams and Tjian, 1991) AGC AGACGTG (SEQ ID NO:33) (downstream element, Burke et al., 1998) GAGCTCTCAGTCTCAGCGATCAA (SEQ ID NO:34).

Of course, those of ordinary skill in the art would be able to produce other examples of the putative promoters in accordance with the methods and techniques provided herein.

Example 4

Design of Promoters

In some embodiments, the present invention provides a plasmid DNA structure used in genetic vaccine and gene therapy (FIG. 1). The components include a selection marker, usually a ampicillin or kanamycin resistant gene; pMB1 relicon for the plasmid replication in E. coli; a mammalian promoter to drive the downstream gene transcription; and a poly-A termination fragment to terminate the transcription of the gene of interest. The poly-A termination often used included bovine growth hormone, human growth hormone or rabbit beta-globulin terminator. The gene of interest could be a reporter gene such as a luciferase gene, or a reporter antigen such as the human alpha-1-antitrypsin (hAAT) gene.

Example 5

Effect of Tata Box Mutation on Promotor Activity

Figure 2:
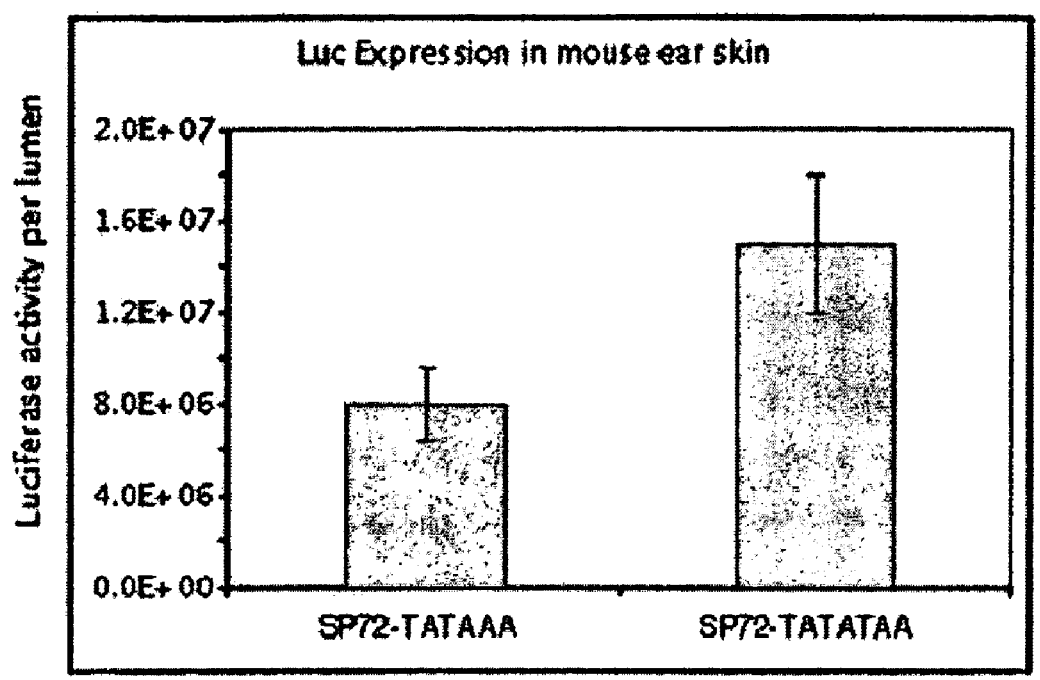
FIG. 2. TATA box mutation reduced the promoter activity by 40%.

In order to optimize the function of the promoter its various versions of TATA boxes were tested for promoter activity. Promoter activity was tested experimentally in mice using ELISA to detect anti-hAAT, and luciferase assays. The highest gene expression level was observed when the TATA box sequence TATATAA (SEQ ID NO:30) was the TFIID binding-site whereas, a mutation by deletion of the third T reduced the promoter activity to about 40% as shown in FIG. 2. This result suggests that at least some mutations of the TATA box sequence affecting the TFIID binding-site decreases promoter activity. One of ordinary skill, following the teachings herein will be able to optimize promoter/enhancers using this information.

Example 6

Effect of Multiple Tata Boxes on Promoter Activity

Figure 3:
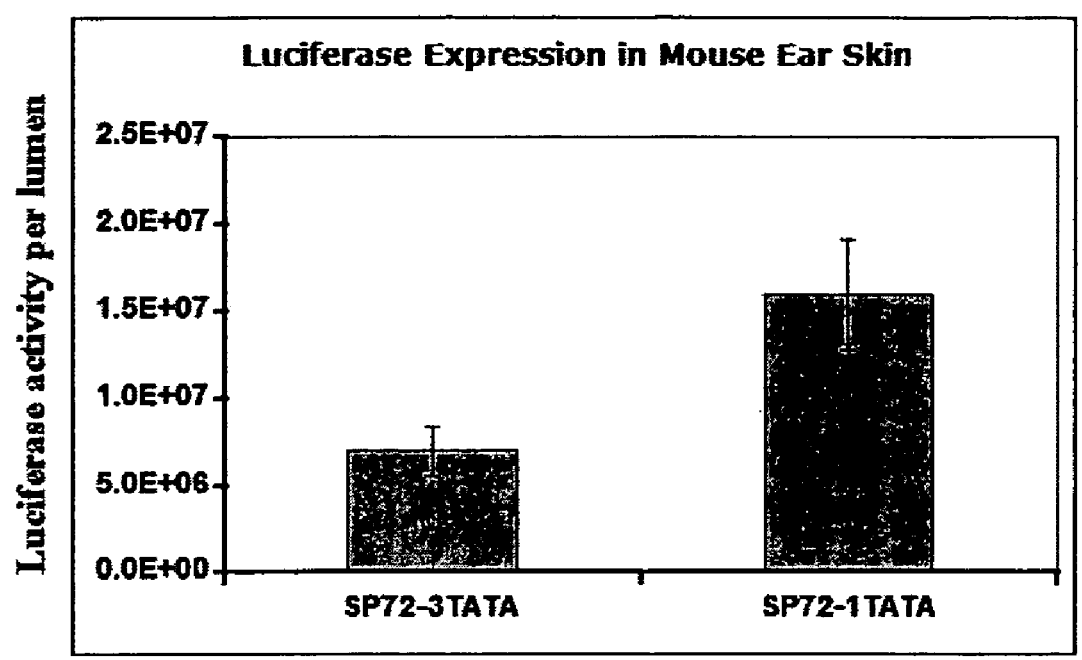
FIG. 3. Multiple TATA boxes reduced the SP promoter activity by about 50%.

In another embodiment of the invention, the effect of multiple TATA boxes on promoter activity was tested. The promoter activity was tested experimentally in mice using ELISA to detect anti-hAAT, and luciferase assays. As demonstrated in FIG. 3, when three TATA boxes (TATATAATATATAATATATAA) (SEQ ID NO:38) are connected instead of a single TATATAA (SEQ ID NO:30) box, the promoter activity is reduced to about 50%. Thus, the number of TATA boxes proved significant in regulating the promoter activity. This result indicates that, in at least some embodiments of the invention a single TATATAA (SEQ ID NO:30) box is required to achieve the highest promoter activity. One of ordinary skill, following the teachings herein will be able to optimize promoter/enhancers using this information.

Example 7

Effect of The Initiator on Promoter Activity

The inventors next determined whether the location of the initiator sequence would improve the promoter activity. Thus, the initiator sequence was placed at various base pairs from the TATA box and the promoter activity was assessed in mice using ELISA to detect anti-hAAT, and luciferase assays. Moving the initiator sequence five base pairs closer to or further away from the TATA box reduced the promoter activity by about 20% (data not shown). Placing the initiator sequence thirty base pairs downstream of the TATA box proved to be the optimum position. Therefore, this result suggests that the location of the initiator from that of the TATATAA box influences the overall promoter activity. One of ordinary skill, following the teachings herein will be able to optimize promoter/enhancers using this information.

Example 8

Effect of The Downstream Element on Promoter Activity

The inventors next determined whether the location of the downstream element would improve the promoter activity. Thus, the downstream element (AGACGTC) was placed at various base pairs from the initiator sequence and the promoter activity was assessed in mice using ELISA to detect anti-hAAT, and luciferase assays. Moving the downstream element five base pairs closer to or further away from the initiator sequence reduced the promoter activity (data not shown). Placing the downstream AGACGTC element thirty base pairs downstream of the initiator sequence increased promoter activity by 15%. Therefore, this result indicates that the location of the downstream element from that of the initiator sequence influences the overall promoter activity. One of ordinary skill, following the teachings herein will be able to optimize promoter/enhancers using this information.

Example 9

Effect of the TFIIB Recognition Element on Promoter Activity

The TFIIB recognition element (GGGCGCC) element is located immediately upstream of the TATA box. Thus, the inventors examined its effect on the activity of the promoter. Promoter activity was assessed in mice using ELISA to detect anti-hAAT, and luciferase assays. Deletion of the TFIIB recognition element was found to reduce the promoter activity by 30% (data not shown). This result suggests that, in order to achieve optimum promoter activity in some embodiments of the invention, the TFIIB recognition element is required. One of ordinary skill, following the teachings herein will be able to optimize promoter/enhancers using this information.

Example 10

Effect of the Transcriptional Elements on Promoter Activity

Various transcription binding sites are located immediately upstream of the core part of the promoter. Some elements' binding sites are grouped together with only 2 to 4 base pairs separating these elements from each other (like SP1, CBP, SP1, NFκB, IFN) immediately upstream of the TATA box. Thus, the inventors examined the effect of these elements on the activity of the promoter by designing binding sites at various base pair distances upstream of the core promoter region, the TATA box.

About 10 base pair distance upstream, a second group of binding sites was designed using AP1, IFN, SP1, c-Jun, and SP1. The distance between the binding sites is 2 to 7 base pairs. Twenty base pair further upstream, a third group of binding sites was designed that included NFκB, AP1, CBP, c-Jun, CREB/ATF, SP1, CBP, and NF1. The distance between the binding sites is about 0- to 4 base pairs. Close to the 5' end of the promoter a fourth group of binding sites was designed that included the ISRE, AP2, Octamer, NF1, AP4, MyB, ATF, and VD binding elements. The distance between the binding sites is about 10 to 30 base pairs. Shortening the promoter to 400 base pairs by deleting 260 bp from the 5' of the promoter reduced the activity by about 20% (data not shown). The overall results of these experiments suggest those transcription elements' binding sites upstream of the promoter influences the promoter activity. One of ordinary skill, following the teachings herein will be able to optimize promoter/enhancers using this information.

Example 11

Activity of the Promoter In VIVO

Figure 4:
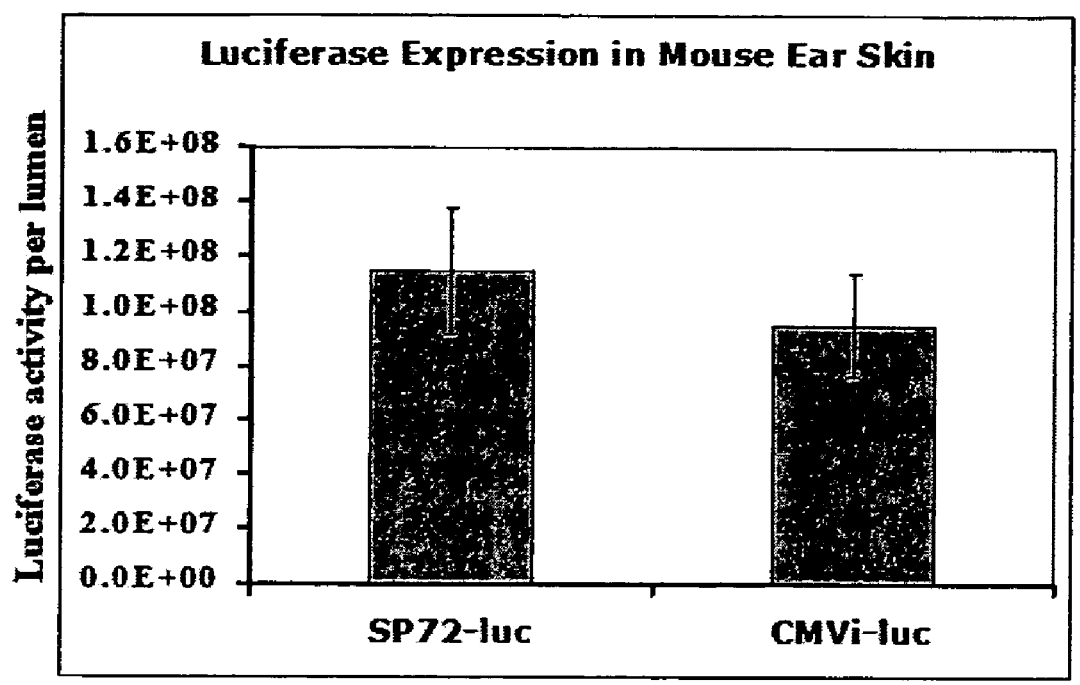
FIG. 4. Luciferase expression in mouse ears after inoculation of SP72-Luc and CMVi-Luc plasmid vector system.

The regulatory activity of the CMV and the exemplary SP72 promoters were compared using luciferase as a reporter in in vivo transfection experiments. Mouse (Balb/c) ears were transfected with 1 µg of DNA-gold mixture using a gene gun. The luciferase activity was measured 24 hours after with BioLumat LB9500 (Berthold, Germany). As shown in FIG. 4, the SP72 promoter drives a slightly (30%) higher gene expression compared to the CMV promoter in a compatible plasmid vector system. The value of the luciferase activity is the mean of four mouse ears (two mice, four ears) in arbitrary units. The result of this experiment indicates that the rationally designed and chemically synthesized SP72 promoter overcomes the caveats of the CMV promoter and is more advantageous for use as a genetic vaccine and gene therapy than the CMV promoter. One of ordinary skill, following the teachings herein will be able to optimize promoter/enhancers using this information.

Example 12

IFN-γ Regulates SP72 Promotor Activity in Colo320 Cancer Cells

Viral promoters have been shown to be down regulated by IFN-γ, TNF and IL-10 (Qin et al., 1997; Harms and Splitter 1995; Ritter et al., 2000). In the present invention, the influence of IFN-γ on SP72 and hCMV-IE promoter activity in transduced human colon carcinoma (COLO 320HSR) cells was investigated. Previously it has been reported that the hCMV-IE promoter, is strongly downregulated by IFN-γ in this colon carcinoma cell line (Harms and Splitter 1995).

Figure 5:
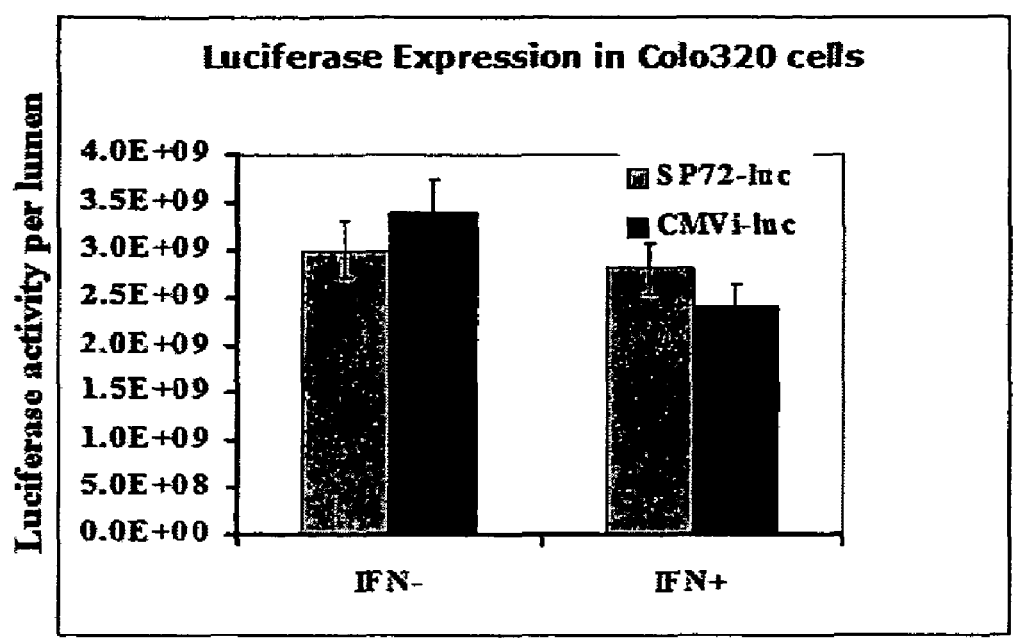
FIG. 5. Luciferase expression in Colo320 cells transfected with SP72-Luc and CMVi-Luc by transIT-LT1 reagent in the absence or presence of IFN-γ.

The cells were grown in a 35-mm plate with about $10^6$ cells per each plate. A polyamine transfection reagent (TransIT-LT1, PanVera Co., Wis.) was used to deliver DNA into cells via transfection. Luciferase activity was measured 24 hours after the transfection. As shown in FIG. 5, neither the CMV promoter nor the SP72 promoter was significantly down-regulated by the addition of IFN.

Example 13

IFN-γ Regulates SP72 Promoter Activity in Raw264-7 Macrophage Cells

Figure 6:
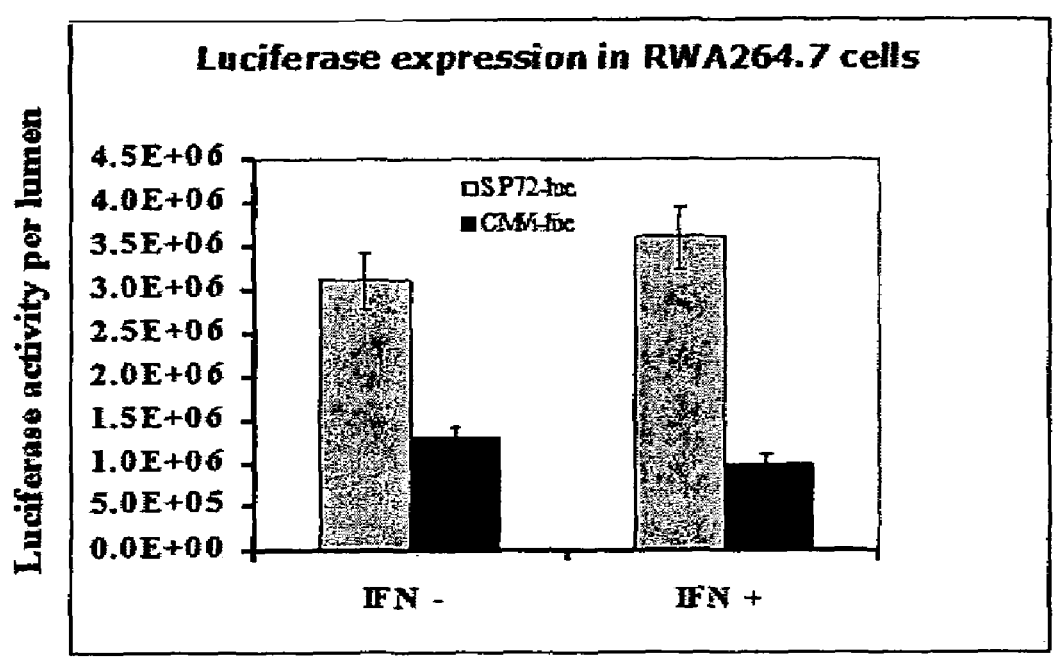
FIG. 6. Luciferase expression in RWA264.7 cells transfected with SP72 Luc and CMVi-Luc by transIT-LT1 reagents in the absence or presence of IFN-γ.

RAW264-7 is a macrophage or monocyte cell line that, similar to the dendritic cells, play an important role in antigen presentation to the immune system. RAW264-7 cells were grown in a 35-mm plate with about $10^6$ cells per plate. A polyamine transfection reagent (TransIT-LT1, PanVera Co., Wis.) was used to deliver DNA into cells via transfection. Luciferase activity was measured 24 hours after the transfection. As shown in FIG. 6, in monocytes such as RAW264-7 cells the SP72 promoter drives a higher level of gene expression (two-fold) than the CMV promoter even in the absence of exogenous interferon. In the presence of interferon, about a three-fold increased level of expression of the luciferase gene was observed with the SP72 promoter compared to the CMV promoter. These results suggest that the SP72 promoter is preferentially expressed in certain cell lines, especially in antigen presenting cells or immune-associated cells. One of ordinary skill, following the teachings herein will be able to optimize promoter/enhancers for appropriate applications using this information.

Example 14

IFN-γ Regulates SP72 Promoter Activity in XS106 Dendritic Cells

Figure 7:
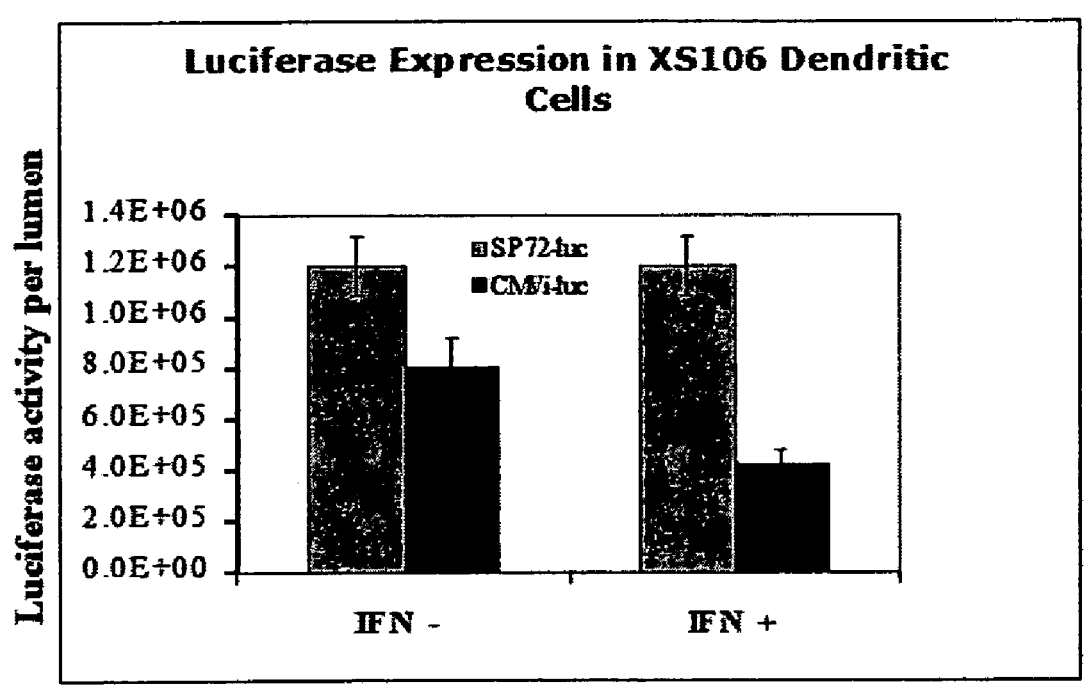
FIG. 7. Luciferase expression in XS106 dendritic cells transfected with SP72-Luc and CMVi-Luc by transIT-LT1 reagents in the absence or presence of IFN-γ.

As demonstrated in RAW264.7 cells (Example 13, FIG. 6), similar observations were further made in mouse dendritic cells XS106 (FIG. 7). Without addition of gamma-interferon to the medium, the SP72 promoter drives a higher (20%) reporter gene expression than the CMV promoter. In the presence of the IFN-γ (1 µg/ml for 24 hours), the CMV promoter activity was significantly inhibited (40% reduction), while SP72 promoter activity was slightly increased 24 hours after transfection of these vectors with TransIT reagent. These results further suggest that the SP72 promoter is preferentially expressed in certain cell lines, specifically in antigen presenting cells.

Example 15

SP72-hAAT Elicits an Immune Response to hAAT Antigen in Mice

This invention further embodies the function of SP72 in eliciting an immune response. A significantly higher immune response to hAAT was observed in mice inoculated with the SP72 promoter vector than with the CMV promoter. SP72-hAAT or CMVi-hAAT plasmid vector (2 µg delivered as two shots per mouse) was inoculated into two group of mice (5 each), by the gene gun method. The antibodies against hAAT were monitored subsequently. A much higher antibody titer (five to six-fold) was observed in the SP72-hAAT group of mice compared to the CMVi-hAAT group of mice during a period of 6 to 8 weeks. Each point represents the mean and standard deviation of 5 mice (FIG. 8).

Figure 8:
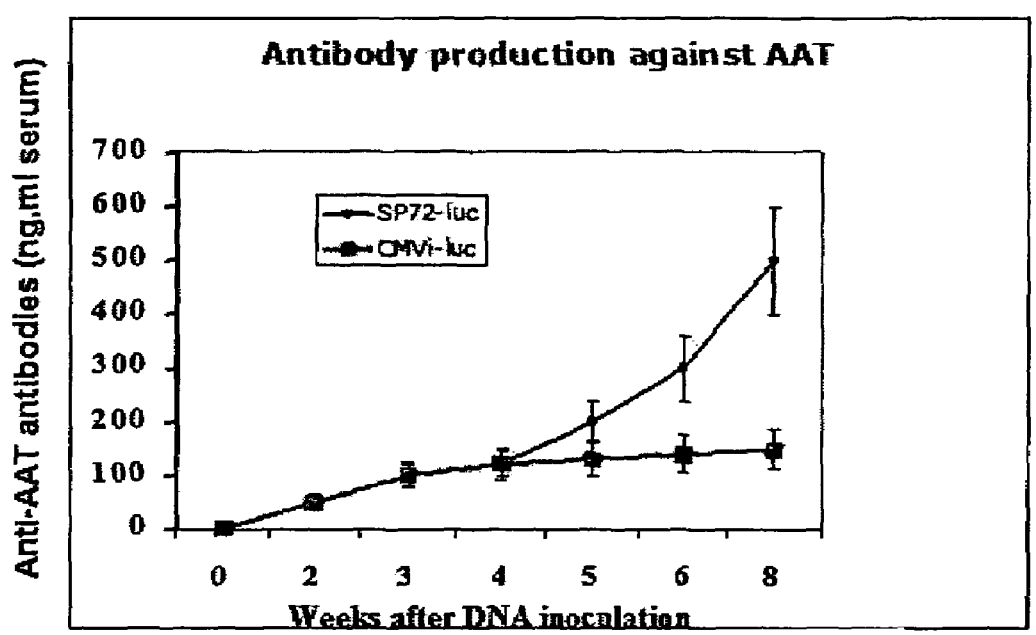
FIG. 8. Immune response to hAAT antigen of the mice immunized with SP72 hAAT and CMVi-hAAT.
Figure 9:
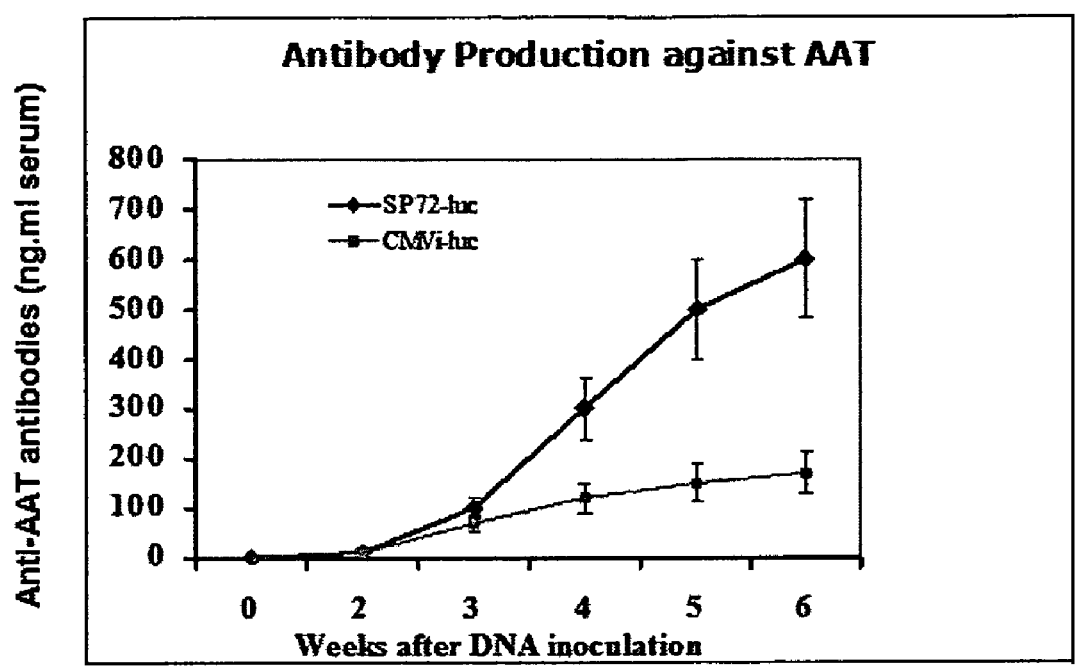
FIG. 9. Immune response to hAAT antigen in mice immunized with SP72-hAAT or CMVi-hAAT.

As demonstrated in FIG. 8, repeated experiments showed that SP72-hAAT consistently elicited a higher level of antibody production than the CMVi-hAAT (FIG. 9). Each point represents mean and standard deviation of 5 mice.

Overall, these results indicate that the SP72 promoter elicits a far greater immune response to an antigen than the CMV promoter.

Example 16

Immune Response to HIV-gp120 is Controlled by the SP72-gp120 Promoter

Figure 10:
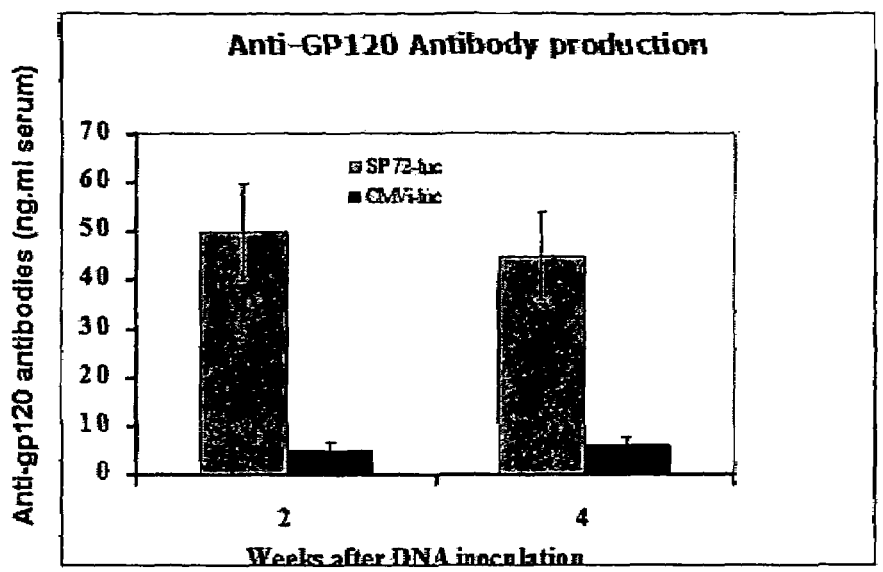
FIG. 10. Immune response to gp120 in mice immunized with SP72-gp120 or CMVi-gp120.

A fragment of about 600 base pairs of the HIV gp120 fragment, HIV 6830-7430 base pairs (including a gp120 fragment of 260-733 base pairs) was cloned, together with a 200 bp ubiquitin leader sequence downstream of the SP72 promoter or the CMV promoter. This resulted in constructs of SP72-gp120 and CMVi-gp120 respectively. In Balb/c mice, a single inoculation with 2 μg of SP72-gp120 using a gene gun elicited a significant antibody production against P18 gp120 peptide, while the mice shot with CMVi-gp120 showed no measurable response. Each group consisted of five mice. Similar to Examples 15, HIV gp-120 elicited a higher immune response controlled by the SP72 promoter than by the CMV promoter (FIG. 10). Thus, this result further indicates that the SP72 promoter elicits a far greater immune response to an immunogenic polypeptide than the CMV promoter.

Example 17

A CTL Response is Elicited Against the SP72-gp120 Peptide

Figure 11:
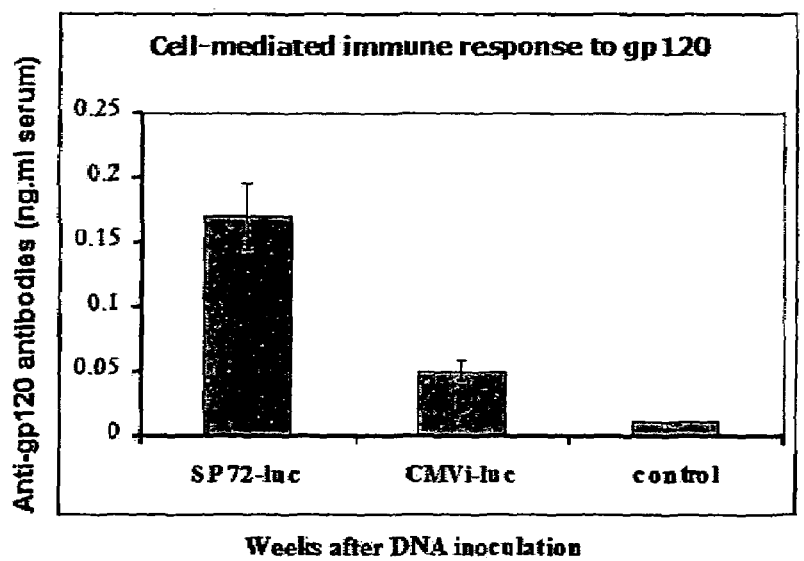
FIG. 11. Release of IFN-γ in stimulated T cells from mice immunized with SP72-gp120 or CMVi-gp120 ($10^4$ T cells/well).

IFN-γ was observed to be released in stimulated T cells after vaccination with SP72-gp120 or CMVi-gp120 ($10^4$ T cells/well; FIG. 11). Peripheral blood T cells of the mice were isolated and stimulated with gp120 peptide to allow the release of interferon gamma. The interferon gamma release in T cells has been associated with cytotoxic activity. This experiment demonstrated that a better antigen-specific cytotoxic T lymphocyte (CTL) response was elicited in the SP72-gp120 vaccinated group of mice. Thus, this result indicates that the SP72 promoter is better than the CMV promoter in eliciting a CTL response agnist an immunogenic peptide.

Example 18

Preparing Vaccines Comprising the SP72 Promoter

As show in FIG. 1, the promoter was inserted into a plasmid vector replacing the CMV promoter/enhancer, and the antigenic sequence was inserted downstream of the SP72 promoter/enhancer. The plasmid vector was amplified in *E. coli* and the DNA was purified using a Qiagen DNA purification kits.

SP72 promoter/enhancer construct with antigenic sequence of choice can be used as vaccine agents for animals including humans. When the plasmid is introduced into the host cells, it will express the antigenic protein and induces an immune response against the antigenic protein. LEE and CEE methods could be applied using the SP72 promoter/enhancer as a gene transcription element.

Example 19

Testing Vaccines Comprising the SP72 Promoter

An SP72 promoter/enhancer construct with an antigenic sequence of choice can be administered to the animal by intramuscular or intradermal injection, gene gun method or microinjector method or any other method known to those in the art. The antibody levels produced in the sera and the CTL response can be monitored using ELISA on peripheral blood. The animals can be challenged with the pathogen against which an immune response is induced. The survival of challenged animals can be compared to that of another group of animals immunized with a CMV promoter/enhancer-based vector.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,682,195
U.S. Pat. No. 4,683,202
U.S. Pat. No. 4,683,202
U.S. Pat. No. 4,684,611
U.S. Pat. No. 4,797,368
U.S. Pat. No. 4,952,500
U.S. Pat. No. 5,139,941
U.S. Pat. No. 5,302,523
U.S. Pat. No. 5,322,783
U.S. Pat. No. 5,384,253
U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,641,515
U.S. Pat. No. 5,645,897
U.S. Pat. No. 5,656,610
U.S. Pat. No. 5,702,932
U.S. Pat. No. 5,703,057
U.S. Pat. No. 5,705,629
U.S. Pat. No. 5,736,524
U.S. Pat. No. 5,767,072
U.S. Pat. No. 5,780,448
U.S. Pat. No. 5,789,215
U.S. Pat. No. 5,846,225

U.S. Pat. No. 5,846,233
U.S. Pat. No. 5,928,906
U.S. Pat. No. 5,945,100
U.S. Pat. No. 5,981,274
U.S. Pat. No. 5,989,553
U.S. Pat. No. 5,994,136
U.S. Pat. No. 5,994,624
U.S. Pat. No. 6,013,516
Ausubel et al., *Current Protocols in Molecular Biology*, John Wiley & Sons, Inc., NY, 1998.
Baichwal and Sugden, In: *Gene Transfer*, Kucherlapati (ed.), NY, Plenum Press, 117-148, 1986.
Barry et al., *Nature*, 377(6550):632-5, 1995.
Blomer et al., *J. Virol.*, 71(9):6641-6649, 1997.
Breathnach and Chambon, *Annu. Rev. Biochem.*, 50:349-83, 1981.
Burke et al., Cold Spring Harbor Symposia on Quantitative Biology, Volume LXIII, The
Mechanisms of Transcription, 1998.
Chen and Okayama, *Mol. Cell. Biol.*, 7:2745-2752, 1987.
Cohen et al, *J. Cell. Physiol.*, 5:75, 1987.
Cotton et al., *Proc. Natl. Acad. Sci. USA*, 89(13):6094-6098, 1992.
Coupar et al., *Gene*, 68:1-10,1988.
Cox et al., *J Virol.*, 67(9):5664-5667, 1993.
Curiel, *Nat. Immun.*, 13(2-3):141-64, 1994.
EP 266,032
Faisst and Meyer., *Nucl. Acids. Res.*, 20:3-26, 1992.
Fechheimer et al., *Proc. Natl. Acad. Sci. USA*, 84:8463-8467, 1987.
Fraley et al., *Proc. Natl. Acad. Sci. USA*, 76:3348-3352, 1979.
Friedmann, *Science*, 244:1275-1281, 1989.
Froehler et al., *Nucleic Acids Res.*, 14(13):5399-5407, 1986.
Fujita et al., *Cell*, 41(2):489-96, 1985.
Fynan et al., *Proc. Natl. Acad. Sci. USA*, 90:11478-11482, 1993.
Gopal, *Mol. Cell Biol.*, 5:1188-1190, 1985.
Graham and van der Eb, *Virology*, 52:456-467, 1973.
Graves et al., *Cell*, 44 (4):565-76, 1986.
Gronostajski, *Nucleic Acids Res.*, 15 (14):5545-59, 1987.
Grunhaus et al., *Seminar in Virology*, 200(2):535-546, 1992
Harland and Weintraub, *J. Cell. Biol.*, 101:1094-1099, 1985.
Harms and Splitter, *Hum. Gene Ther.*, 6(10):1291-1297, 1995.
Hermonat and Muzyczka, *Proc. Natl. Acad. Sci. USA*, 81:6466-6470, 1984.
Horwich et al. *J. Virol.*, 64:642-650, 1990.
Hu et al., *Genes Dev.*, 4(10):1741-52, 1990.
Kadonaga et al., *Cell*, 51 (6):1079-90, 1987.
Kaneda et al., *Science*, 243:375-378, 1989.
Kato et al., *J. Biol. Chem.*, 266:3361-3364, 1991.
Kelleher and Vos, *Biotechniques*, 17(6):1110-7, 1994.
Laughlin et al., *.J. Virol.*, 60(2):515-524, 1986.
Le et al., *Vaccine*, 18(18):1893-901, 2000.
Lebkowski et al., *Mol. Cell Biol.*, 8(10):3988-3996, 1988.
Levenson et al., *Hum. Gene Ther.*, 20;9(8):1233-1236, 1998.
Liu et al., *Cell*, 61(7):1217-24, 1990.
Maniatis et al., Molecular Cloning, A Laboratory Manual, Cold Spring Harbor Press, Cold Spring Harbor, N.Y., 1990.
Mann et al., *Cell*, 33:153-159, 1983.
McDonnel and Askari, *New Engl. J. Med.*, 334(1)42-45, 1996.
McLaughlin et al., *J. Virol.*, 62(6):1963-1973, 1988.
Miller et al., *Am J. Clin. Oncol.*, 15(3):216-221, 1992.
Mitchell et al., *Science*, 245(4916):371-8, 1989.
Muzyczka, *Curr. Top Microbiol. Immunol.*, 158:97-129, 1992.
Naldini et al, *Science*, 272(5259):263-267, 1996.
Nicolas and Rubenstein, In: *Vectors: A survey of molecular cloning vectors and their uses*, Rodriguez and Denhardt (eds.), Stoneham: Butterworth, 493-513, 1988.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-28, 1993.
Pardoll and Beckerleg, *Immunity*, 3:165-169, 1995.
Paskind et al., *Virology*, 67:242-248, 1975.
PCT Application WO 94/09699
PCT Application WO 95/06128
Perlmann et al., *Genes Dev.*, (7B):1411-22, 1993.
Pollock et al., *Genes Dev.*, 5(12A):2327-41, 1991.
Potrykus et al., *Mol. Gen. Genet.*, 199(2):169-177, 1985.
Potter et al., *Proc. Natl Acad. Sci. USA*, 81:7161-7165, 1984.
Qin et al., *Hum. Gene Ther.*, 8 (17):2019-2029, 1997.
Remington's Pharmaceutical Science", 15th Ed., pg. 1035-1038 and 1570-1580.
Ridgeway, In: *Vectors: A survey of molecular cloning vectors and their uses*, Rodriguez and Denhardt, eds., Stoneham, Butterworth, 467-492, 1988.
Rippe et al., *Mol. Cell Biol.*, 10:689-695, 1990.
Ritter et al., *Cytokine*, 12(8):1163-1170, 2000.
Robinson, *Can. Med. Assoc. J.*, 152(10):1629-1632, 1995.
Ruvkun et al., *Cell*, 64(3):475-8, 1991.
Sambrook et al., In: *Molecular Cloning: A Laboratory Manual*, 2d Ed., Cold Spring Harbor Laboratory Press, Cold Spring Harbor, N.Y., 2000.
Saxena et al., *Bioscience*, 28(1):129-34, 2003.
Smale and Baltimore, *Cell*, 57(1):103-113, 1989.
Spooner et al., *Gene Therapy*, 2:173-180, 1995.
Tanaka et al., *Mol Cell Biol.*, 13(8):4531-8, 1993.
Tang et al., *Nature*, 356:152-154, 1992.
Temin, In: *Gene Transfer*, Kucherlapati (ed.), NY, Plenum Press, 149-188, 1986.
Tomic et al., *Nucl. Acids Res.*, 12:1656, 1990.
Tratschin et al., *Mol. Cell. Biol.*, 4:2072-2081, 1984.
Tur-Kaspa et al., *Mol. Cell Biol.*, 6:716-718, 1986.
Ulmer et al., *Science*, 259:1745-1749, 1993.
Upender et al., *Biotechniques*, 18:29-31, 1995.
Virbasius et al., *Genes Dev.*, 7(12A):2431-45, 1993.
Wang et al., In: *Animal Cell Technology: Basic and Applied Aspects*, Kaminogawa et al, Kluwer Academic Publishers, Netherlands, 5:463-469, 1993.
Whitton et al., *J. Virol.*, 67:(1)348-352,1993.
Williams et al., *Genes Dev.*, 5(4):670-82, 1991.
Wong et al., *Gene*, 10:87-94, 1980.
Wu and Wu, *J. Biol. Chem.*, 262:4429-4432, 1987.
Wu and Wu, *Biochem.*, 27:887-892, 1988.
Yen et al., *Proc Natl Acad Sci. USA.*, 88(12):5077-81, 1991.
Zufferey et al., *Nat. Biotechnol.*, 15(9):871-875, 1997.

What is claimed is:

1. A synthetic promoter sequence comprising the sequence of SEQ ID NO:35.

2. The synthetic promoter sequence of claim 1, further defined as comprising the sequence of SEQ ID NO:36.

3. The synthetic promoter sequence of claim 1, further defined as comprising the sequence of SEQ ID NO:37.

* * * * *

SEQUENCE LISTING

<160> NUMBER OF SEQ ID NOS: 37

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
cggtacatga tgttctcgat gcaatatcac gtgaaggtca aaaataggtc a           51

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
aggtcacctc tctcggct                                                18

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
atcaaataag agtgtaggga cgggagaggg ggaaaacaga acagaacagt gctgacgtca  60

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gcaggcagtt g                                                       11

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ccctttgaaa acgttaacgt taacgttcag ctgcagctgc a                      41

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 6 gctgattaa                                                            9

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
taattacagc caa                                                       13

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
aggcgccaaa ggcaacgtta tatgcaaata tgcaaa                              36

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tgagaacagg ggggggggc gg                                              22

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
acatcggttc aacgtttctg gtttcaattt ctcttct                             37

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
attaataatt accgttggcc attagcca                                       28

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 12 tatccaat                                                              8

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13 ggggcggg                                                              8

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
atttgacgtc a                                                         11

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15 ataatgac                                                              8

<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16 gccaat                                                                6

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
agggactttc c                                                         11

<210> SEQ ID NO 18
<211> LENGTH: 7
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 18 gactcac                                                                    7

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19 ggggatttc                                                                  9

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
caacgttttg gttgacgaa                                                      19

<210> SEQ ID NO 21
<211> LENGTH: 8
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21 atgggcgg                                                                   8

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
tgtaaatgac ata                                                            13

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ggaaaactga ctca                                                           14

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 24
caaagggaga agtga                                                15

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
aagtgggact ttcc                                                 14

<210> SEQ ID NO 26
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26 aaagggcgg                                                       9

<210> SEQ ID NO 27
<211> LENGTH: 5
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27 ccaat                                                           5

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
tgtgggcggg g                                                    11

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
ccaccggtgt tcctgaaggg cgcc                                      24

<210> SEQ ID NO 30
<211> LENGTH: 7
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 30 tatataa                                                                  7

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31 ggggggcgg gcgcgttcgt cctcattc                                            28

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
tggaccgcgt ccgccccgcg                                                    20

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
agcagacgtg                                                               10

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
gagctctcag tctcagcgat caa                                                23

<210> SEQ ID NO 35
<211> LENGTH: 190
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
aaatgacata ggaaaactga ctcacaaagg gagaagtgaa agtgggactt tccaaagggc        60
ggccaattgt gggcgggggcc accggtgttc ctgaagggcg cctatataag ggggggcggg      120
cgcgttcgtc ctcattctgg accgcgtccg ccccgcgagc agacgtggag ctctcagtct       180
cagcgatcaa                                                              190
```

<210> SEQ ID NO 36
<211> LENGTH: 614
<212> TYPE: DNA
<213> ORGANISM: Artificial Sequence
<220> FEATURE:
<223> OTHER INFORMATION: Description of Artificial Sequence: Synthetic Primer

<400> SEQUENCE: 36

```
cggtacatga tgttctcgat gcaatatcac gtgaaggtca aaataggtc aaggtcacct      60
ctctcggcta tcaaataaga gtgtagggac gggagagggg gaaaacagaa cagaacagtg     120
ctgacgtcag caggcagttg ccctttgaaa acgttaacgt taacgttcag ctgcagctgc     180
agctgattaa taattacagc caaaggcgcc aaaggcaacg ttatatgcaa atatgcaaat     240
gagaacaggg ggggggggcg gacatcggtt caacgtttct ggtttcaatt tctcttctat     300
taataattac cgttggccat tagccatatc caatgggcg ggatttgacg tcaataatga      360
cgccaatagg gactttccga ctcacgggga tttccaacgt tttggttgac gaaatgggcg     420
gtgtaaatga cataggaaaa ctgactcaca aaggagaag tgaaagtggg actttccaaa      480
gggcggccaa ttgtgggcgg ggccaccggt gttcctgaag gcgcctata taggggggg      540
cgggcgcgtt cgtcctcatt ctggaccgcg tccgccccgc gagcagacgt ggagctctca     600
gtctcagcga tcaa                                                       614
```

<210> SEQ ID NO 37
<211> LENGTH: 596
<212> TYPE: DNA
<213> ORGANISM: Artificial Sequence
<220> FEATURE:
<223> OTHER INFORMATION: Description of Artificial Sequence: Synthetic Primer

<400> SEQUENCE: 37

```
cggtacatga tgttctcgat gcaatatcac gtgaaggtca aaataggtc aatcaaataa      60
gagtgtaggg acgggagagg gggaaaacag aacagaacag tgctgacgtc agcaggcagt    120
tgccctttga aaacgttaac gttaacgttc agctgcagct gcagctgatt aataattaca    180
gccaaaggcg ccaaaggcaa cgttatatgc aaatatgcaa atgagaacag ggggggggg     240
cggacatcgg ttcaacgttt ctggtttcaa tttctcttct attaataatt accgttggcc    300
attagccata tccaatgggg cgggatttga cgtcaataat gacgccaata gggactttcc    360
gactcacggg gatttccaac gttttggttg acgaaatggg cggtgtaaat gacataggaa    420
aactgactca caaagggaga gtgaaagtg ggactttcca aagggcggcc aattgtgggc     480
ggggccaccg gtgttcctga agggcgccta tataagggggg ggcgggcgcg ttcgtcctca    540
ttctggaccg cgtccgcccc gcgagcagac gtggagctct cagtctcagc gatcaa        596
```